United States Patent
Kannan et al.

(10) Patent No.: US 12,065,684 B2
(45) Date of Patent: Aug. 20, 2024

(54) DEMAND SYNTHESIS OF POLYNUCLEOTIDE SEQUENCES

(71) Applicant: CODEX DNA, INC., San Diego, CA (US)

(72) Inventors: Krishna Kannan, San Diego, CA (US); John E. Gill, San Marcos, CA (US); Daniel G. Gibson, Carlsbad, CA (US); Lixia Fu, San Diego, CA (US)

(73) Assignee: TELESIS BIO INC., San Diego, CA (US)

(*) Notice: Subject to any disclaimer, the term of this patent is extended or adjusted under 35 U.S.C. 154(b) by 187 days.

(21) Appl. No.: 17/320,021

(22) Filed: May 13, 2021

(65) Prior Publication Data

US 2021/0355519 A1 Nov. 18, 2021

Related U.S. Application Data

(60) Provisional application No. 63/025,696, filed on May 15, 2020.

(51) Int. Cl.
*C12P 19/34* (2006.01)

(52) U.S. Cl.
CPC .................. *C12P 19/34* (2013.01)

(58) Field of Classification Search
CPC ............... C12P 19/34; C12Q 1/6806; C12Y 301/13003; C12Y 302/02028; C12Y 605/01001
See application file for complete search history.

(56) References Cited

U.S. PATENT DOCUMENTS

| | | | |
|---|---|---|---|
| 10,059,929 B2 | 8/2018 | Efcavitch et al. | |
| 2004/0146901 A1 | 7/2004 | Morris et al. | |
| 2012/0259607 A1 | 10/2012 | Hillson | |
| 2013/0225446 A1 | 8/2013 | Wu et al. | |
| 2013/0309725 A1 | 11/2013 | Jacobson et al. | |
| 2015/0051088 A1 | 2/2015 | Kim | |
| 2015/0159152 A1 | 6/2015 | Allen et al. | |
| 2016/0215316 A1* | 7/2016 | Pedersen | C12N 15/1031 |
| 2016/0340670 A1 | 11/2016 | Lou et al. | |
| 2017/0081660 A1 | 3/2017 | Cox et al. | |
| 2017/0267998 A1* | 9/2017 | Weiner | C12N 15/1031 |
| 2018/0137418 A1 | 5/2018 | Roquet et al. | |
| 2018/0163254 A1 | 6/2018 | Gill et al. | |
| 2020/0283756 A1 | 9/2020 | Vladar et al. | |
| 2021/0277446 A1 | 9/2021 | Gill et al. | |
| 2021/0355519 A1 | 11/2021 | Kannan et al. | |

FOREIGN PATENT DOCUMENTS

| | | | |
|---|---|---|---|
| WO | WO 2005/111236 | 11/2005 | |
| WO | WO 2017/096322 | 6/2017 | |
| WO | WO-2017096322 A1 * | 6/2017 | .............. C12M 1/34 |
| WO | WO 2019/241290 | 12/2019 | |

OTHER PUBLICATIONS

Thoo, Paul Kong, and Daniel M. Brown. "Synthesis of oligodeoxyribonucleotides containing degenerate bases and their use as primers in the polymerase chain reaction." Nucleic acids research 20.19 (1992): 5149-5152 (Year: 1992).*
Zhu, Zhenyu, et al. "Engineering strand-specific DNA nicking enzymes from the type IIS restriction endonucleases BsaI, BsmBI, and BsmAI." Journal of molecular biology 337.3 (2004): 573-583 (Year: 2004).*
Nørholm, Morten HH. "A mutant Pfu DNA polymerase designed for advanced uracil-excision DNA engineering." BMC biotechnology 10 (2010): 1-7 (Year: 2010).*
Cobb, Ryan E., Yajie Wang, and Huimin Zhao. "High-efficiency multiplex genome editing of Streptomyces species using an engineered CRISPR/Cas system." ACS synthetic biology 4.6 (2015): 723-728 (Year: 2015).*
Nord, Karin, et al. "A combinatorial library of an a-helical bacterial receptor domain." Protein Engineering, Design and Selection 8.6 (1995): 601-608 (Year: 1995).*
Olufsen, Magne, Arne O. Smalås, and Bjørn O. Brandsdal. "Electrostatic interactions play an essential role in DNA repair and cold-adaptation of uracil DNA glycosylase." Journal of molecular modeling 14 (2008): 201-213 (Year: 2008).*
Zimmerman (Proceedings of the National Academy of Sciences 80.19 (1983): 5852-5856) (Year: 1983).*
Pingoud (Cellular and molecular life sciences 62 (2005): 685-707) (Year: 2005).*
Worl (Tetrahedron 55.10 (1999): 2941-2956) (Year: 1999).*
Sebastian Palluk et al., "De novo DNA synthesis using polymerase-nucleotide conjugates," Nature Biotechnology, advanced online publication, doi:10.1038/nbt.4173.
PCT International Search Report and Written Opinion in International Application No. PCT/US2021/03244, dated Sep. 15, 2021, 11 pages.
PCT International Search Report and Written Opinion in International Application No. PCT/US2021/059422, dated May 5, 2022, 15 pages.
PCT International Search Report and Written Opinion in International Application No. PCT/US2022/48407, dated Mar. 8, 2023, 14 pages.

* cited by examiner

*Primary Examiner* — Nancy J Leith
*Assistant Examiner* — Kyle T Rega
(74) *Attorney, Agent, or Firm* — Richard San Pietro

(57) ABSTRACT

The invention provides methods of synthesizing a product DNA molecule having a desired and/or defined sequence. The methods involve annealing at least one long oligonucleotide and at least one short oligonucleotide to at least one anchor strand having a sequence at least partially complementary to the at least one long and at least one short oligonucleotide. The invention also provides methods of synthesizing DNA molecules by assembling oligonucleotide members of a library that contains less than 20,000 members that can be assembled into all possible DNA sequences.

37 Claims, 8 Drawing Sheets
Specification includes a Sequence Listing.

| Sequence# | Sequence | GC content (%) |
|---|---|---|
| SEQ ID NO: 1 | ATTTATTACTAGACAGAGGA | 30 |
| SEQ ID NO: 2 | AGGCAGAGTTAATTCGAACA | 40 |
| SEQ ID NO: 3 | AGACTGGTACAACAGGACTC | 50 |
| SEQ ID NO: 4 | CGCGGTCCAACTTAGGCGTA | 60 |

FIG. 6

DEMAND SYNTHESIS OF POLYNUCLEOTIDE SEQUENCES

CROSS-REFERENCE TO RELATED APPLICATIONS

This application claims benefit of priority under 35 U.S.C. § 119(e) of U.S. Ser. No. 63/025,696, filed May 15, 2020, the entire contents of which is incorporated herein by reference in its entirety.

INCORPORATION OF SEQUENCE LISTING

The material in the accompanying sequence listing is hereby incorporated by reference into this application. The accompanying sequence listing text file, name CODEX2260-1_SL.txt, was created on May 2, 2023 and is 19800 bytes. The file can be accessed using Microsoft Word on a computer that uses Windows OS.

FIELD OF THE INVENTION

The invention relates to synthetic biology and the assembly of polynucleotide molecules from a library of oligonucleotide parts.

BACKGROUND OF THE INVENTION

The fields of synthetic biology and gene editing and therapeutics have a continuing and growing need for oligonucleotides of diverse and known sequences. Existing methods for synthesizing small oligonucleotides involve chemical synthesis via solid-phase, sequential coupling of nucleotides to generate the oligonucleotide of desired length and sequence. Oligonucleotides produced are then released from the solid phase, deprotected, and collected for assembly into larger oligonucleotides by other methods. While automated, these processes are subject to side reactions and base errors, thus limiting the length of the oligonucleotides produced. For applications requiring ultra-high sequence fidelity, these methods have additional limitations.

Enzymatic methods of synthesizing oligonucleotides also exist and involve the use of enzymes such as terminal deoxynucleotidyl transferase (TdT), a template-independent polymerase that catalyzes the incorporation of deoxyribonucleotides into the 3'-hydroxyl end of DNA templates. But the enzyme shows strong bias for specific nucleotide bases and does not reliably add nucleotides in the desired order and length.

There is a continuing need for methods of synthesizing oligonucleotides efficiently and with high fidelity so that the user can produce oligonucleotides of any desired length and sequence.

SUMMARY OF THE INVENTION

The invention provides methods of synthesizing a product DNA molecule having a desired and/or defined sequence. The methods involve annealing at least one long oligonucleotide and at least one short oligonucleotide to at least one anchor strand having a sequence at least partially complementary to the at least one long and at least one short oligonucleotide. After annealing, at least one long oligonucleotide bound to an anchor strand abuts at least one short oligonucleotide bound to the same anchor strand. The anchor strand has one or more non-standard nucleotides, and optionally one or more degenerate nucleotides. The method involves ligating the abutting at least one long oligonucleotide and at least one short oligonucleotide to form a dsDNA molecule. The dsDNA molecule is contacted with one or more enzymes that degrade DNA comprising non-standard nucleotides and the product DNA molecule is thereby synthesized. The invention also provides methods of synthesizing DNA molecules by assembling oligonucleotide members of a library that contains less than 20,000 members that can be assembled into all possible DNA sequences.

In a first aspect the invention provides a method of synthesizing a product DNA molecule having a desired sequence. The method involves annealing at least one long oligonucleotide and at least one short oligonucleotide to at least one anchor strand(s) having a sequence at least partially complementary to the at least one long and at least one short oligonucleotide. After annealing, at least one long oligonucleotide bound to an anchor strand abuts at least one short oligonucleotide bound to the same anchor strand. The at least one anchor strand has one or more non-standard nucleotides, and optionally one or more degenerate nucleotides. The method further involves ligating the abutting at least one long oligonucleotide and at least one short oligonucleotide to form a dsDNA molecule comprising non-standard nucleotides, and contacting the dsDNA molecule with one or more enzymes that degrade DNA comprising one or more non-standard nucleotides to thereby synthesize the product DNA molecule.

In one embodiment the annealing occurs within a binding set comprising two long oligonucleotides, two short oligonucleotides, and two anchor strands, and further comprising ligating the two short oligonucleotides to the two long oligonucleotides, wherein the long and short oligonucleotides further comprise variable nucleotides. The annealing can occur within a binding set comprising two long oligonucleotides, one short oligonucleotide, and at least one anchor strand, and wherein the short oligonucleotide is ligated to two long oligonucleotides, and the short oligonucleotide and two long oligonucleotides comprise variable nucleotides. In any embodiment the non-standard nucleotide can be deoxy-uridine. The dsDNA molecule can have the non-standard nucleotides on only one strand.

In any embodiment the method can also include a step of amplifying the product DNA molecule using a DNA amplification method. In any embodiment the method can include performing multiple cycles of PCR on the product DNA molecule. The product DNA molecule can have flanking sequences for annealing a primer used in the multiple cycles of PCR. In any embodiment the product DNA molecule can be 8-30 nucleotides in length. The ligation can be performed by a DNA ligase. In one embodiment the at least one long oligonucleotide is from 12-24 nucleotides in length, and the at least one short oligonucleotide is from 3-8 nucleotides in length. In another embodiment the at least one long oligonucleotide is from 12-24 nucleotides in length, and the at least one short oligonucleotide is from 3-8 nucleotides in length, and the at least one anchor strand is from 20-60 nucleotides in length.

In any embodiment the method can include a step of ligating in solution two DNA molecules having double-stranded ends by blunt end ligation and according to the desired sequence. In one embodiment after annealing, a first short oligonucleotide abuts a first long oligonucleotide, and a second short oligonucleotide abuts a second long oligonucleotide, and the method involves ligating the first short and long oligonucleotides, and ligating the second short and long oligonucleotides.

In another embodiment after annealing the at least one short oligonucleotide abuts a first long oligonucleotide and a second long oligonucleotide, and the method involves ligating the at least one short oligonucleotide to the first and second long oligonucleotides. In various embodiments the one or more enzymes that degrade DNA comprising non-standard nucleotides are one or more enzymes selected from uracil DNA glycosylase, Endonuclease VIII, and Exonuclease T.

In any embodiment each anchor strand has 4-6 variable and/or 4-6 degenerate nucleotides present in a single degenerate region. In any embodiment the long and short oligonucleotides each have 4-6 variable nucleotides. In one embodiment the two long oligonucleotides also have variable nucleotides that bind to the degenerate nucleotides on their respective at least partially complementary anchor strands during the annealing step. In one embodiment the long oligonucleotides, short oligonucleotides, and anchor strand each comprise 4-6 variable nucleotides.

In some embodiment the product DNA molecule can be single-stranded DNA or double-stranded DNA 8-30 nucleotides in length, not including the flanking sequences. In other embodiments the product DNA molecule is single-stranded DNA or double-stranded DNA 16-20 oligonucleotide in length.

In any embodiment the long oligonucleotides and short oligonucleotides can be provided to the method from an oligonucleotide library. In some embodiments the short oligonucleotides provided from the oligonucleotide library are 3-7 nucleotides in length. The oligonucleotide library can include long oligonucleotide members having all four possible nucleotides at each position of a variable nucleotide. The long oligonucleotides can have a variable region that anneals to the sequence of degenerate nucleotides on the one or more anchor strands.

In any embodiment of the method the short and long oligos comprise 4-6 variable nucleotides, the anchor strands comprise 4-6 degenerate nucleotides, the anchor strands comprise at least two deoxy-uridine monophosphate nucleotides, and the product DNA molecule is amplified by PCR.

In any embodiment the product DNA molecule can have an error rate of fewer than 1 in 25,000. In any embodiment the at least one long oligonucleotide, at least one short oligonucleotide, and at least one anchor strand can be selected from an oligonucleotide library having less than 20,000 members, which oligonucleotide library can contain oligonucleotides sufficient to synthesize all possible nucleotide sequences.

In any embodiment the methods can also involve a step of contacting the product DNA molecule with a Type IIS restriction endonuclease to generate a product DNA molecule having single-stranded overhangs. The Type IIS restriction endonuclease can be any, for example BsaI and/or BsmBI. In one embodiment the product DNA molecule encodes a non-genetic message. The product DNA molecule can have a sequence corresponding to bytes of information. In any embodiment the multiple cycles of PCR can include a first step of PCR using primers having non-standard nucleotides set two nucleotides back from the 3' end of the primer.

In one embodiment the product DNA molecule can encode a gRNA, and the flanking sequences can encode one or more transcriptional elements. In any embodiment the transcriptional elements can be any one or more of a promoter, a Cas9 handle, and a terminator.

In another aspect the invention provides a method of synthesizing a product DNA molecule. The method involves providing a library of oligonucleotides wherein the library of oligonucleotides has fewer than 20,000 oligonucleotide members, and the oligonucleotide members in the library can be assembled into all possible polynucleotide sequences; and assembling oligonucleotide members from the library to obtain the product DNA molecule. In one embodiment the library of oligonucleotides is present on a solid phase and the oligonucleotide members are present at defined physical locations within the library of oligonucleotides. The solid phase can be a DNA chip. The product DNA molecule can be a double-stranded DNA 8-30 base pairs in length. The product DNA molecule can be subjected to continuing methods to ligate the product DNA molecule with at least one additional DNA molecule to produce a larger product DNA molecule. In some embodiments the library has fewer than 16,000 oligonucleotide members. The larger product DNA molecule can be at least 1,000 bp in length. The product DNA molecule can have an error rate of fewer than 1 in 10,000.

In one embodiment assembling oligonucleotide members involves annealing at least one long oligonucleotide and at least one short oligonucleotide to at least one anchor strand(s) having a sequence at least partially complementary to the at least one long and at least one short oligonucleotide, and after annealing, at least one long oligonucleotide bound to an anchor strand abuts at least one short oligonucleotide bound to the same anchor strand, and the at least one anchor strand can have one or more non-standard nucleotides, and optionally one or more degenerate nucleotides; and ligating the abutting at least one long oligonucleotide and at least one short oligonucleotide to form a dsDNA molecule having non-standard nucleotides; and contacting the dsDNA molecule with one or more enzymes that degrade DNA having one or more non-standard nucleotides to thereby synthesize the product DNA molecule.

In another aspect the invention provides a kit containing a library of 20,000 or less (fewer) oligonucleotide members, where the oligonucleotide members in the library can be assembled into every possible polynucleotide sequence. The oligonucleotide members of the kit can be isolated at defined locations and spatially separated. In one embodiment the library is present on a DNA chip.

In another aspect the invention provides an oligonucleotide library having less than 20,000 defined locations and having an oligonucleotide library member at each location. The oligonucleotide library members can be assembled into every possible polynucleotide sequence. In one embodiment polynucleotide sequence is less than 10 Mbp in length.

DESCRIPTION OF THE DRAWINGS

FIG. 5 discloses SEQ ID NOS 51-63 and 68.

FIG. 6 provides a schematic illustration of an embodiment of the invention for storing digital information in DNA. A 16 bp product DNA molecule is produced encoding four bytes of information. The examples shows how a non-genetic message (here "cat in a hat") can be encoded into DNA using the methods of the invention. FIG. 6 discloses SEQ ID NOS 51-54 and 64-67.

DETAILED DESCRIPTION OF THE INVENTION

Figure 1A:
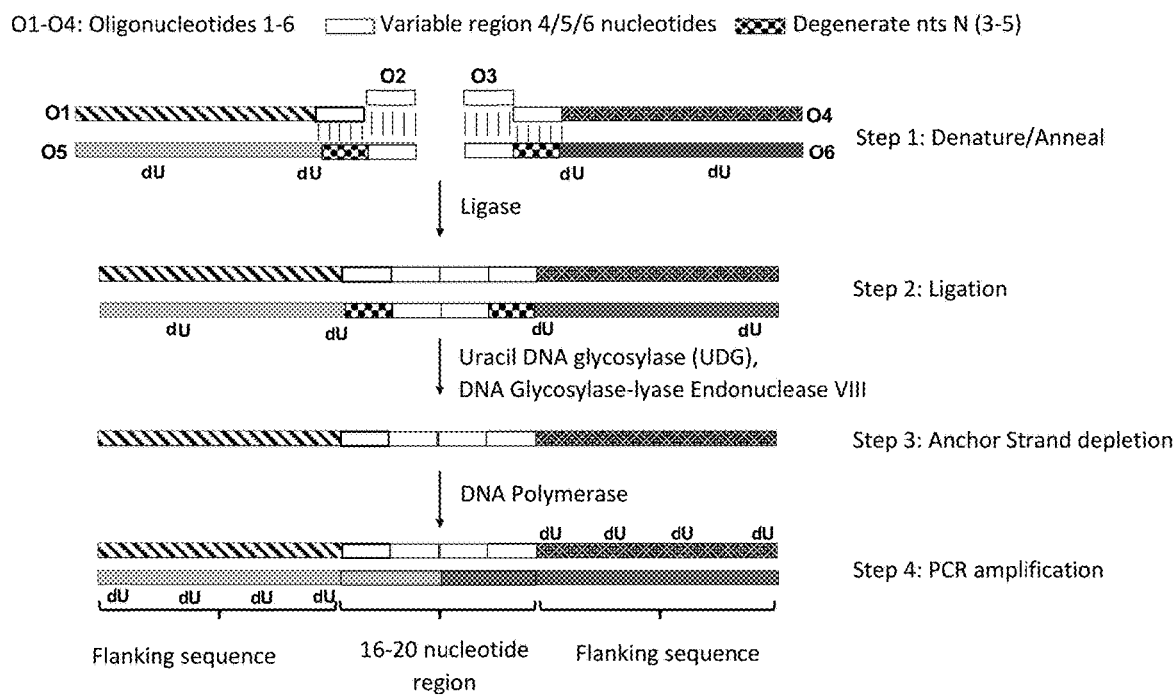
FIG. 1a provides a schematic illustration of an embodiment of the invention termed Embodiment 1 (E1) using two short oligos and two long oligos and two anchor strands. O2 and O3 are short oligonucleotides composed of variable nucleotides. O2 binds to the variable region of O5 and O3 binds to the variable region of O6.

The invention provides methods of assembling DNA molecules of any sequence with high fidelity using a library of oligonucleotides. The methods involve the use of an oligonucleotide library having DNA molecule members such that all possible DNA sequences can be assembled from the library using the methods. In one embodiment the library of oligonucleotides has less than 20,000 members.

Many efforts have been made towards achieving methods of assembling any possible DNA sequence from a library having a limited number of members. The present inventors discovered that any possible DNA sequence can be conveniently assembled using the materials and methods disclosed herein. The invention therefore enables creation of a library of less than 20,000 oligonucleotides, from which all possible oligonucleotide sequences can be assembled. The library of less than 20,000 oligonucleotides can be conveniently provided on a small device (e.g. a DNA chip), and devices and instrumentation provided to selectively assembly any DNA sequence using only the members of the oligonucleotide library.

In some embodiments the invention provides methods of synthesizing oligonucleotides of 8-30 nucleotides in length that can be used as building blocks for further assembly into larger oligonucleotides. The invention also provides a library of pre-made oligonucleotides, which can contain less than 20,000 members. The invention also provides methods of synthesizing DNA molecules by assembling oligonucleotides from the library. The members of the library can be assembled into all possible DNA sequences. Kits for conducting the methods are also provided. The invention does not rely on TdT (terminal deoxynucleotidyl transferase) enzyme, nor require its base-by-base synthesis of oligonucleotides.

Oligo Library

In various embodiments the oligonucleotide members in the library can be DNA of various lengths. The library can have long and short oligonucleotide members. In various embodiments the library of oligonucleotides can have less than 50,000 members, or less than 40,000 members, or less than 30,000 members, or less than 20,000 members or less than 19,000 members or less than 18,000 members or less than 17,000 members or less than 16,000 members. The methods are able to synthesize all possible polynucleotide sequences using the oligonucleotide members in the library. In various embodiments the invention permits the assembly of over 4 billion (for a 16mer) and up to over 1 trillion (for a 20mer) polynucleotides beginning only with those oligonucleotides in the library. In various embodiments each oligonucleotide in the library can be used from 100 to 10,000 times in the synthesis of product DNA molecules. The product DNA molecule assembled can be of any size, for example it can be less than 1 Mbp or less than 5 Mbp or less than 10 Mbp or less than 12 Mbp, or less than 13 Mbp, or less than 14 Mbp, or less than 15 Mbp or 1-10 Mbp, or 1-12 Mbp, or 1-15 Mpb. The terms "oligo" and "oligonucleotide" are used interchangeably herein, and indicates a polymer of nucleotides of generally short length. "Polynucleotide" is a general term denoting a polymer of nucleotides of any length.

In other embodiments the methods can also be used with even smaller libraries to assemble a significant number of sequences that may be desired, for example the library can have fewer than 14,000 members or fewer than 12,000 members, or fewer than 10,000 members or fewer than 8,000 members, or fewer than 7,000 members, and be used to assemble a more limited and directed number of sequences in a defined category where such sequences are needed. Examples of a defined category can include a set of genes related to a specific biological function, or from a particular organism. Examples of defined categories can include (but are not limited to), genes or sequences related to transcription, regulation, RNA metabolism, translation, protein folding, protein export, RNA (rRNA, tRNA, small RNAs), ribosome biogenesis, rRNA modification, DNA replication, DNA repair, DNA topology, DNA metabolism, chromosome segregation, cell division, and tRNA modification.

In any embodiment the product DNA molecule synthesized in the method can be synthesized entirely or only from oligonucleotides from the oligonucleotide library. The oligo library can thus contain short oligonucleotides, long oligonucleotides, and anchor strands.

Long and Short Oligonucleotides

In one embodiment the long and short oligonucleotides can be DNA of any length, but the long oligonucleotides are of greater length than the short oligonucleotides. For example, the short oligonucleotides can be up to 12 nucleotides in length, and the long oligonucleotides can be greater than 12 nucleotides in length. In various embodiments short oligonucleotides can have many lengths, examples include without limitation 4-6 nucleotides (nt), or 3-8 nt or 4-7 nt or 4-8 nt or 5-7 nt or 5-8 nt or 6-7 nt or 6-8 nt. In various embodiments long oligonucleotides can have a length of, for example and without limitation, 9-18 nt or 9-20 nt or 9-22 nt or 9-25 nt or 9-30 nt or 9-35 nt or 10-18 nt or 10-20 nt or 10-22 nt or 11-18 nt or 11-20 nt or 11-22 nt or 20-24 nt or 20-25 nt. Long and short oligonucleotides can be present in any combination or sub-combination of short and long oligonucleotide lengths provided herein.

In any embodiment the long oligonucleotides can be of greater length than the longest short oligonucleotide, for example the short oligonucleotides are 5-12 nucleotides in length, and the long oligonucleotides are at least 13 nucleotides in length. Thus, the long oligonucleotides can be long relative to the short oligonucleotides. In any embodiment the short and/or long oligonucleotides can have only nucleotides having no non-standard bases. In any embodiment the short and/or long oligonucleotides can have only nucleotides having standard bases, i.e. all nucleotides in the oligonucleotide have a base that is either A (adenine), T (thymine), C (cytosine), or G (guanine). Long oligonucleotides and/or anchor strands can have sequences for binding a primer, which can be used in PCR or another DNA amplification procedure.

FIG. 1a depicts oligonucleotides and methods utilized in one embodiment of the invention. In this embodiment oligos 1-6 (O1-O6) all are depicted as having a variable region. O1 and O4 are long oligonucleotides and O2 and O3 are short oligonucleotides. O5 and O6 are anchor strands having non-standard nucleotides, indicated as deoxyuridine (dU). In Step 1 O1 and O2 anneal to O5, and O3 and O4 anneal to O6. This annealing can be simultaneous but in some embodiments does not have to be simultaneous. O2 can anneal to O5, and O3 can anneal to O6 and the long oligonucleotides can anneal subsequently. But oligos can anneal in any order. In this embodiment a long oligonucleotide and a short oligonucleotide each anneal so that they abut one another and are annealed to the same anchor strand. In any embodiment blunt end ligation can occur. A double-stranded DNA molecule is formed comprised of O1-O6, and therefore contains one strand of DNA having one or more non-standard nucleotides, which can all be on the same one of the two strands. In another step anchor strand depletion can occur. The anchor strand has one or more non-standard nucleotides, which contain a non-standard base. The dsDNA is contacted with one or more enzymes that degrade or digest DNA having one or more non-standard nucleotides. Degrading or digesting the DNA can involve excising one or more non-standard nucleotides (or the bases from those nucleotides), eroding the strand having the non-standard nucleotides and leaving a single-stranded DNA molecule, which can have no non-standard bases or only standard bases. The single-stranded DNA molecule can then optionally be amplified by PCR or another DNA amplification procedure, such as by contacting the single-stranded DNA molecule with primers and subjecting the mixture to PCR or another DNA amplification procedure. Primers used in PCR or other DNA amplification procedures can have one or more non-standard nucleotides (e.g. dU), in a similar or the same manner as anchor strands. O1, O4, O5 and O6 can have sequences for binding one or more primers suitable to accomplish the DNA amplification procedure, and which can be present as flanking sequences.

Figure 1B:
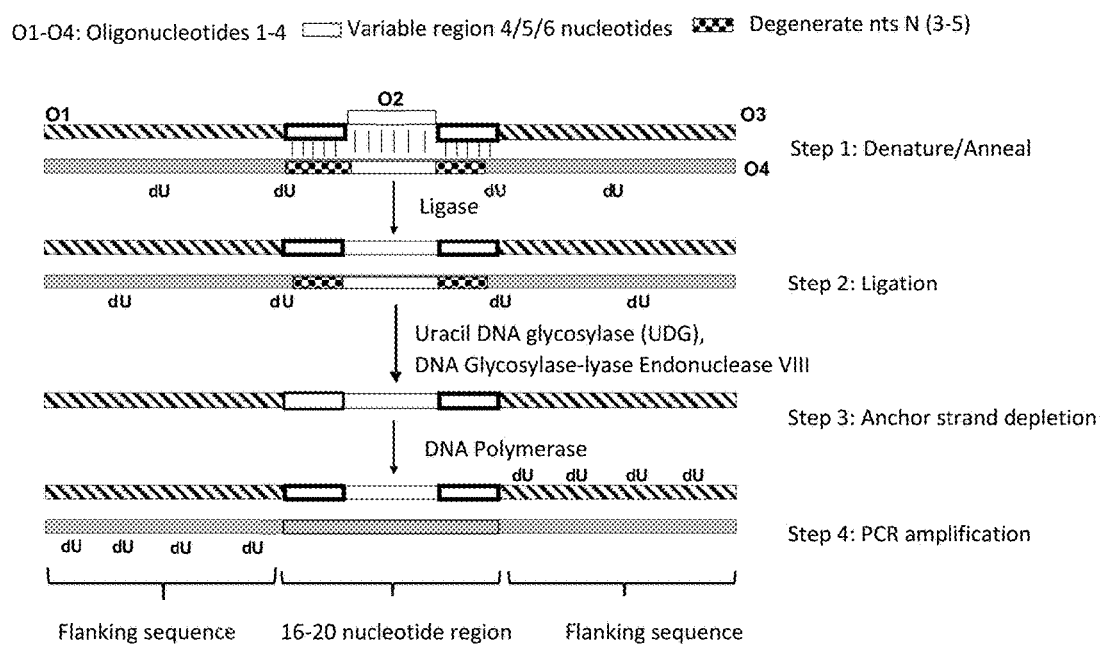
FIG. 1b provides a schematic illustration of an embodiment of the invention termed Embodiment 2 (E2) using one short oligo and two long oligos and one anchor strand. dU are depicted as part of the oligonucleotide sequence. O2 binds to the variable region of O4.
Figure 2:
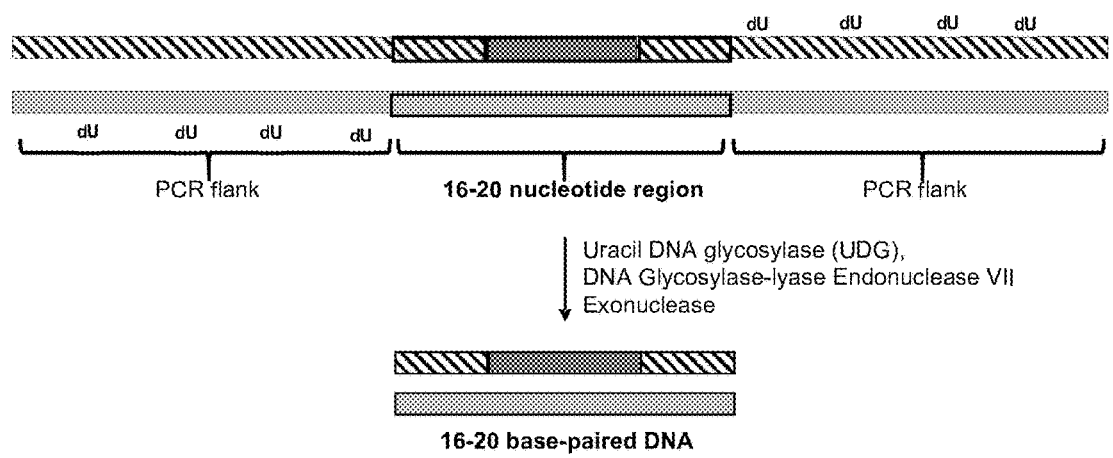
FIG. 2 depicts an embodiment for the removal of flanks. Following the PCR reaction the dsDNA produced has 16-20 nucleotides of defined sequence flanked by universal primer sites for PCR. In this embodiment deoxy-uridine is the non-standard nucleotide, and degrading or digesting the anchor strand involves contact with uracil DNA glycosylase (UDG), and DNA Glycosylase-Endonuclease III and Exonuclease, resulting in an 8-30 nucleotide dsDNA of defined sequence. dU are depicted as part of the oligonucleotide sequence.

FIG. 1b depicts another embodiment (Embodiment 2, E2). In this embodiment oligos 1-4 (O1-O4) all are depicted as having a variable region. O1 and O3 are long oligonucleotides and O2 is a short oligonucleotide. O4 is an anchor strand having non-standard nucleotides. In Step 1 O1, O2, and O3 anneal to O4. Again, this annealing may be, but does not have to be, simultaneous and O1, O2, and O3 can anneal in any order to O4. In this embodiment blunt end ligation does not occur and is not necessary. Thus, in some embodiments (including additional embodiments not depicted in FIG. 1b) the methods do not involve blunt end ligation and blunt end ligation does not occur. A double-stranded DNA molecule is formed comprised of O1-O4, and therefore contains one strand of DNA having one or more non-standard nucleotides from O4. In another step anchor strand depletion can occur. The anchor strand O4 has one or more non-standard nucleotides, which contain a non-standard base. The dsDNA is contacted with one or more enzymes that degrade or digest DNA having one or more non-standard nucleotides. Degrading or digesting the DNA can involve excising one or more non-standard nucleotides (or the bases from those nucleotides), eroding the strand having the non-standard nucleotides and leaving a single-stranded DNA molecule. The single-stranded DNA molecule can then be amplified by PCR or another DNA amplification procedure, such as by contacting the single-stranded DNA molecule with primers and subjecting the mixture to PCR or another DNA amplification procedure. O1, O3, and O4 in the embodiment can have sequences for binding one or more primers suitable to accomplish the DNA amplification procedure.

Anchor Strands

In some embodiments the anchor strands can comprise one or more non-standard nucleotides. Non-standard nucleotides are nucleotides having a nucleobase other than C, G, A, or T. In some embodiments the non-standard nucleotide has uracil as a nucleobase (e.g. deoxy-uridine monophosphate). An AP site (also known as an abasic site) is a location in DNA that has neither a purine nor a pyrimidine base (nor a derivative of them), thus a nucleobase is missing; these are also a type of non-standard base. Other examples of non-standard nucleotides include, but are not limited to, dihydroxythymine, thymine glycol, an AP site, an apurinic site, an apyrimidinic site, 5-hydroxy-5-methylhydantoin, 5-hydroxy-hydantoin, and methyltartronylurea. Persons of ordinary skill in the art with reference to this disclosure will realize other non-standard nucleotides that will find use in the invention. As used herein deoxynucleotide can refer to the monophosphate, diphosphate, or triphosphate form. Thus, deoxyuridine can indicate any of dUMP, dUDP, or dUTP, which will be understood by the person of ordinary skill in the art through context of usage.

In some embodiments the anchor strands have one or more uracil-containing nucleotides as a non-standard nucleotide. Optionally the anchor stands can also have one or more degenerate nucleotides, which can be present as a degenerate nucleotide region. In some embodiments the uracil-containing nucleotide contains deoxy-uracil, but in other embodiments the uracil-containing nucleotide can contain uracil glycol as a nucleobase. Uracil-containing non-standard nucleotides can also occur from cytosine deamination or incorporation of deoxyuridine phosphate residues. Such uracil-containing nucleotides can be incorporated into the anchor strand in some embodiments. In various embodiments an anchor strand can have 2 or 3 or 4 or 5 or 6 or more than 6 dU nucleotides in its sequence. In some embodiments the non-standard nucleotides can be spaced approximately evenly in the anchor strand. In various embodiments the anchor strand is an oligonucleotide that can have a uracil-containing nucleotide every 7 or every 8 or every 9 or every 10 or every 12 or every 15 nucleotides. While spaced non-standard nucleotides are sufficient, anchor strands can also have one or more consecutive non-standard nucleotides, in addition to or instead of spaced non-standard nucleotides. Anchor strands can be of any suitable length depending on the application, but in various embodiments the anchor strand can be 20-30 nucleotides in length, or 25-30 nucleotides in length, or can be from 25-40 or from 25-85 nucleotides or from 25-80 nucleotides or from 25-70 nucleotides, or from 25-65 nucleotides, or from 25-60 nucleotides in length. But in other embodiments the anchor strands can also be 18-65 or 18-85 or 20-65 or 20-85. In various embodiments of Embodiment 1 (E1) (FIG. 1a) the anchor strands can be 20-35 nucleotides or 20-30 nt or 25-30 nt in length. In various embodiments of Embodiment 2 (E2) (FIG. 1b) the anchor strands can be 30-40 nucleotides or 30-55 or 40-60 nucleotides in length. In any embodiment the anchor strand can be about the length of a long oligo and a short oligo combined, or 80-120% or 90-110% of the length of a long oligo and a short oligo combined. In any embodiment the anchor strand can be about the length of two long oligos and one short oligo combined, or 80-120% or 90-110% of the length of two long oligos and one short oligo combined.

Various embodiments using different length of short oligos, long oligos, and anchor strands can be utilized. In various embodiments of E1 or E2 (FIGS. 1a and 1b) the short oligonucleotides can be 4-6 nucleotides in length and the long oligonucleotides can be 14-22 nt in length. In other embodiments of E1 the short oligonucleotides can be 5-6 nucleotides in length and the long oligonucleotides can be 14-22 nt in length; anchor strands can be 20-30 nt in length. In another embodiment the short oligonucleotides are 4-6 or 5-6 nucleotides in length and the long oligonucleotides are 16-20 nt in length; anchor strands can be 20-35 nt in length. In some embodiments of E2 the short oligonucleotides are 4-6 or 5-6 nucleotides in length and the long oligonucleotides are 16-20 nt in length; anchor strands can be 40-60 nt in length. Persons of ordinary skill with resort to this disclosure will realize that the length of short oligos, long oligos, and anchor strands can be adjusted depending on the specific application contemplated.

In any embodiment a DNA sequence containing one or more non-standard nucleotide(s) is a substrate for one or more enzyme(s) that degrade DNA containing non-standard nucleotide(s). When the non-standard nucleotide is a uracil-containing nucleotide it can be a substrate for the one or more enzymes that degrade DNA containing uracil-containing nucleotide(s). In one embodiment the enzyme is uracil DNA glycosylase (UDG), which catalyzes the hydrolysis of the N-glycosidic bond from deoxyuridine to release uracil. The uracil-containing nucleotide can also be a substrate for endonuclease VIII, which has DNA glycosylase activity and AP lyase activity—thus, the endonuclease VIII can cleave uracil from the nucleotide. In one embodiment USER© II can be utilized to excise uracil (New England Biolabs, Ipswich, MA). USER© II has uracil DNA glycosylase activity (which excises a uracil base) and Endonuclease III having lyase activity (which breaks the phosphodiester backbone at the 3' and 5' sides of the abasic site), thus promoting the degradation of DNA. The uracil-containing nucleotide can also be a substrate for Endonuclease VIII, which has N-glycosylase activity and an AP-lyase activity. Endonuclease VIII can also be used when the non-standard nucleotide is a damaged pyrimidine, which it will cleave to leave an apurinic site. Endonuclease VIII can be used in various embodiments where the non-standard base is any of urea, 5,6-dihydroxythymine, thymine glycol, 5-hydroxy-5-methylhydantoin, uracil glycol, 6-hydroxy-5,6-dihydrothymine, or methyl tartronylurea. Endonuclease III can also recognize and remove nucleotides having these non-standard bases. An exonuclease (e.g. exonuclease T, exonuclease I, and others) can be used to remove single-stranded overhangs. Persons of ordinary skill with resort to this disclosure will realize many other non-standard bases and manners of degrading DNA containing them, which will find application in the present invention.

Anchor strands are at least partially complementary to at least one short oligonucleotide and at least one long oligonucleotide. In some embodiments the anchor strands are fully complementary to at least one short oligonucleotide and/or at least one long oligonucleotide. Anchor strands can, optionally, have 4, 5, 6, 7, 8, or 4-6 or 4-7 or 4-8 or more than 8 degenerate nucleotides, which can be present as a consecutive sequence or dispersed singly or in groups in the molecule. A "region" of degenerate nucleotides is two or more consecutive degenerate nucleotide locations.

Methods

The methods of the invention synthesize a product DNA molecule having a desired sequence, which can be a predetermined sequence, i.e. one decided by the user prior to beginning the method. In various embodiments the product DNA molecule of desired sequence can be 16-20 nucleotides in length, or 6-12 or 6-16 or 6-20 or 6-24 or 12-24 nucleotides in length, or 12-25 or 12-30 or 12-40 or 12-60 or 20-25 or 20-30 or 20-40 or 20-60 or 20-80 or 60-120 or 60-180 nucleotides in length. The product DNA molecule can be optionally assembled having flanking sequences, useful for continuing procedures (e.g. PCR or other DNA amplification). Flanking sequences can be of any length appropriate for the continuing procedures contemplated, for example about 12 nucleotides, or about 18 nucleotides, or about 18-22 nucleotides or 18-30 nucleotides or 18-60 nucleotides. The methods involve annealing at least one long oligonucleotide and at least one short oligonucleotide to at least one anchor strand(s) having a sequence at least partially complementary to the at least one long and at least one short oligonucleotide. In any embodiment the long and short oligo(s) can be completely complementary to a portion of the anchor strand(s). The annealing can be a partial annealing where only at least 50% or at least 70% or at least 90% of the nucleotides in the short and/or long oligonucleotides are annealed to their complementary nucleotides on the at least one anchor strand, or can be a complete annealing where all of the nucleotides in the short oligonucleotide and/or long oligonucleotide are annealed to the complementary sequence on the at least one anchor strand. After annealing the at least one long oligonucleotide bound to an anchor strand abuts at least one short oligonucleotide bound to the same anchor strand. In some embodiments the at least one long oligonucleotide can abut two short oligonucleotides bound to the anchor strand, and/or the at least one short oligo can abut two long oligos bound to the anchor strand. The at least one long oligo and the at least one short oligo can be annealed or bound to the same anchor strand. In one embodiment at least one short oligo is abutted by two long oligos and is annealed between the two long oligos, where the short and long oligos are annealed to an anchor strand. In any embodiment the terms binding to the same anchor strand, or any two oligos in the methods being "bound," can mean direct binding, or can refer to two polynucleotides that are annealed, or to polynucleotides bound by hydrogen bonding. The hydrogen bonding can be of a strength sufficient to hold the two polynucleotides together in the steps of the methods disclosed herein (e.g. at 25° C. for at least 2 minutes).

The at least one long and at least one short oligonucleotide that abut one another and are annealed to the same anchor strand can be ligated to form a double-stranded DNA molecule (dsDNA). The ligation can be performed by a ligase, for example T4 DNA ligase, but any suitable DNA ligase can be utilized in the invention (e.g. Taq ligase). The dsDNA molecule can then be contacted with one or more enzymes that degrade DNA comprising uracil-containing nucleotides to synthesize the product DNA molecule.

The methods therefore allow the production of a product DNA molecule of 8-30 or 8-40 or 8-50 or 8-60 or 8-70 nucleotides (not counting flanking sequences) in length without the need for a conventional oligonucleotide synthesizer, which typically relies on chemical synthesis (e.g. phosphoramidite chemistry). Instead, the methods rely on enzymatic synthesis, and therefore such oligonucleotides of 8-30 or 8-40 or 8-50 or 8-60 or 8-70 or 8-80 or 8-100 nucleotides in length after removal of flanking sequences can therefore be produced on demand. In other embodiments the methods can produce a product DNA molecule of 6-30 or 6-40 or 6-70 or 6-90 or 6-120 nucleotides, not counting flanking sequences.

The methods can also involve performing multiple cycles of PCR or another DNA amplification procedure on the product DNA molecule. PCR is known to those of ordinary skill in the art and involves the use of primers. In any embodiment primers used in PCR or other DNA amplification procedures can contain one or more dU nucleotides, or other non-standard nucleotides. In some embodiments the primers can have two or three or four or more than four dU nucleotides, or other non-standard nucleotides.

In any embodiment the methods are performed without the use of restriction enzymes. In any embodiment the methods also can be performed without cloning or the need for cloning. In any embodiment the methods can be performed entirely in vitro. In any embodiment the methods can be performed without the use of live cells in any step of the method. In any embodiment the methods can produce a scarless product DNA molecule. By scarless DNA is meant DNA that does not have any nucleotide(s) introduced by or from the process of synthesizing the DNA (e.g. residue nucleotides from a linker or flanking sequence). In any embodiment the methods can produce a product DNA molecule that is barcode free, or free of a nucleotide sequence placed for identification purposes. A barcode can be a sequence that is not otherwise needed but has a particular sequence and is used to identify a sequence of DNA. In various examples and embodiments a barcode sequence is 6-8 nucleotides in length, or 4-10 nucleotides in length. In any embodiment the methods can be performed without any part of any oligonucleotide used in the method being immobilized, i.e. bound to a solid phase or solid support (e.g. a bead, DNA chip, microfluidic surface, etc). In any embodiment the oligonucleotides can be annealed in solution, and can be ligated in solution, i.e. without any oligonucleotide in the step or method being bound or partially bound to a solid phase or solid support. In any embodiment the methods of the invention can synthesize the product DNA molecule according to the methods described herein without the use of and without performing chemical assembly techniques (e.g. phosphoramidite chemistry). In any embodiment the methods of the invention can assemble the product DNA molecule using only enzymatic assembly of oligonucleotides. In any embodiment the methods can be performed by drawing the short oligonucleotides, long oligonucleotides, and anchor oligonucleotides from a library comprising less than 20,000 members, or from any library described herein. In any embodiment the at least one long oligonucleotide, at least one short oligonucleotide, and at least one anchor strand can be selected from an oligonucleotide library having less than 20,000 members, or from any oligo library described herein.

FIG. 1a illustrates an embodiment of the invention involving blunt end ligation. In some embodiments a short oligonucleotide can anneal to an anchor strand to form a DNA molecule that has a blunt end, and optionally is partially single-stranded and partially double-stranded. For example with reference to FIG. 1a, O2 can anneal to O5 to form such a DNA molecule being partially single-stranded and partially double-stranded and having a blunt end; correspondingly, O3 can anneal to O6 to form another such molecule. In any embodiment two blunt-end double-stranded DNA molecules (whether partially or fully double-stranded), for example O2-O5 and O3-O6 (or O1-O2-O5 and O3-O4-O6) depicted in FIG. 1a, can be joined in solution in a blunt end ligation by a DNA ligase to form a longer DNA molecule. Binding of long oligonucleotides O1 and O4 so that O1 and O2 abut one another, and O3 and O4 abut one another can also occur. Subsequent ligation of abutting oligonucleotides by contacting the oligos with a DNA ligase can form the DNA molecule. Thus, in some embodiments formation of the product DNA molecule can involve one or more steps of blunt-end ligation of two at least partially double-stranded DNA molecules. However, in other embodiments O1 and O2 can anneal with O5 to form abutting O1 and O2 (O1-O2-O5), and O3 and O4 can anneal with O6 to form abutting O3 and O4 (O3-O4-O6), and the DNA molecules formed can be ligated in solution by blunt end ligation through the action of a DNA ligase to form the DNA molecule.

Thus, in one embodiment a long oligonucleotide and a short oligonucleotide can both be bound to the same anchor strand to form a blunt end DNA molecule, and can be optionally ligated together, and can then be joined by blunt end ligation to another long and short oligonucleotide that are both bound to a different anchor strand and also form a blunt end DNA molecule. In any embodiment the anchor strand can be longer than the short oligo and the long oligo and no longer than the combined lengths of both the short oligo and the long oligo. Note that the anchor strands have non-standard bases (dU in FIG. 1). The ligated dsDNA can be contacted with enzymes that degrade DNA having non-standard bases, e.g. UDG and Endonuclease III or DNA glycosylase-lyase Endonuclease VIII. When the anchor strand is depleted a single-stranded DNA molecule is left.

As illustrated in FIG. 1b, in some embodiments a short oligonucleotide and two long oligonucleotides can anneal to the same anchor strand, and the short oligonucleotide can be annealed to the anchor strand in between and abutting the two long oligonucleotides. The two long oligos, short oligo, and anchor strand can be a binding set, and the binding set can be optionally partly single-stranded and partly double-stranded. With reference to FIG. 1b, O1 and O3 are long oligonucleotides, O2 is a short oligonucleotide, and O4 is an anchor strand. O1-O3 can bind in any order to anchor strand O4. The two long oligos and one short oligo can be bound to the anchor strand O4 where O2 is in between and abutting O1 and O3. O2 can be ligated (e.g. by ligase) to O1 and O3 after the oligos have bound to anchor strand O4. O2 can also spontaneously ligate to O1 and O3.

The product DNA molecule can optionally be formed having flanking sequences to the 3' and 5' sides of the product DNA molecule. These flanking sequences in one embodiment can provide binding sites for primers in amplification procedures (e.g. by PCR). The flanking sequences can optionally also have non-standard nucleotides for removal later. Thus, the product DNA molecule will predominate and be synthesized in the method. In some embodiments the product DNA molecule will contain flanking sequences having the primer binding sites. In any embodiment the methods can include a step of removing flanking sequences after amplification to yield the product DNA molecule. Methods of removing flanking sequences are known in the art. One such method is found in US 2018/0163254, published Jun. 14, 2018, which is hereby incorporated by reference in its entirety, including all tables, figures, and claims. In some embodiments the flanking sequences can be utilized to add length to the product DNA molecule, or to surround the product DNA molecule with transcriptional elements or other beneficial sequences that will be utilized in the final product. For example, the flanking sequences can be set to provide a promoter in front of the product DNA molecule, and/or to provide a terminator. In one embodiment the product DNA molecule is a 16-20 bp gRNA sequence, and the flanking sequences can be set to provide a promoter in front of the gRNA sequence, and a Cas9 handle and terminator after it. Thus, in some embodiments the product DNA molecule can be expanded to encompass the flanking sequences as well, which can provide more utility than being only binding sites for primers.

Any of the methods disclosed herein can be performed in an automated method, for example by an automated instrument. An automated method is one where no human intervention is necessary after the method is initiated—the method goes to completion from that point without a human having to perform any action. The automated instrument can contain components for selecting oligonucleotide members from the oligo library. A DNA sequence to be assembled can be uploaded, recorded on, or stored on a non-transitory computer-readable medium. A non-transitory computer-readable medium can be programmed to execute automated steps when inserted into or otherwise in electronic communication with a processor attached to or comprised within the automated instrument. The automated steps can be those disclosed herein for performing a method disclosed herein. Thus, the invention also provides a non-transitory computer-readable medium that is programmed with the locations of each member of an oligonucleotide library described herein, where the oligonucleotide library is present on a suitable support structure for the oligo library. In one embodiment the non-transitory computer-readable medium is programmed with the locations of 14,000-20,000 or 15,000-20,000 or 16,000-20,000, or up to 20,000, or 14,000-25,000 oligonucleotide library members. The medium can also be programmed with instructions to combine 4-6 members of a binding set from the library and to assemble the members of the binding set into a product DNA molecule according to the methods described herein.

The invention also provides kits having an oligo library described herein located on a medium. The medium can be any suitable medium, for example one or more of a DNA chip, one or more bead(s), one or more of a 96 well plate, one or more of a 384 well plate, one or more microfluidic reaction support(s), one or more microtiter plate(s), one or more nanotiter plate(s), one or more picotiter plate(s), or other solid support or solid phase surface that can retain oligonucleotide members of the library. When more than one medium is utilized the media can be present in numbers sufficient to accommodate the oligo library. The medium containing the oligonucleotide library can contain members in any suitable volume, and examples include volumes of 1 nl up to 100 ul, or 10 nl up to 100 ul. A DNA chip (or DNA microarray) is a solid surface having a collection of microscopic locations, to which oligonucleotides can be attached and/or stored.

The methods of the invention can synthesize a product DNA molecule with a very low error rate. In various embodiments the methods can produce any product DNA molecule described herein with error rates of less than 1 in 10,000 nucleotides, or less than 1 in 12,000 nucleotides, or less than 1 in 15,000 nucleotides, or less than 1 in 25,000 nucleotides, or less than 1 in 30,000 nucleotides, or less than 1 in 40,000 nucleotides, or less than 1 in 50,000 nucleotides.

In any embodiment the methods disclosed herein do not utilize or require the use of a vector in the methods.

Binding Sets

A binding set is a group of oligonucleotides where each oligonucleotide in the set can bind to at least one other oligonucleotide in the set in a method of synthesizing a product DNA molecule as described herein. In one embodiment a binding set contains two long oligonucleotides, two short oligonucleotides, and two anchor strands (e.g. the binding set depicted in FIG. 1a). In another embodiment a binding set can contain two long oligonucleotides, one short oligonucleotide, and at least one anchor strand (e.g. as depicted in FIG. 1b). In other embodiments a binding set can contain a long oligo and a short oligo and an anchor strand having sequences complementary to both. Binding sets can be bound to other binding sets to form a larger DNA molecule or to form the product DNA molecule of desired sequence. However, persons of ordinary skill with resort to this disclosure will realize that other binding sets utilizing other combinations of oligonucleotides can be assembled and be effective for assembling the product DNA molecule according to the methods described herein, or variations of them. For example, a binding set could utilize more than two anchor strands, or more than two long oligonucleotides, or more than two short oligonucleotides. Additional binding sets that can be utilized in the methods are also described herein. Such alternative embodiments of binding sets can be annealed so that at least one long oligonucleotide and at least one short oligonucleotide anneal to an anchor strand, and the at last one long oligonucleotide abuts at least one short oligonucleotide bound to an anchor strand.

These are only exemplary binding sets that can find use in the methods and should not be considered limiting. In other embodiments a binding set can contain three or four or five or six short oligos and two or three or four long oligos. In any embodiment multiple anchor strands can be used. In only some examples three or four or five or six anchor strands can be utilized in a binding set and find use in the methods disclosed herein. In only some exemplary embodiments four short oligos can be applied with two long oligos and one or two anchor strands. Short oligos, long oligos, and anchor strands can therefore be applied in any combination, and the person of ordinary skill with resort to this disclosure will be able to arrive at multiple combinations of oligos and anchor strands that can be applied in the methods.

Variable Regions

In various embodiments short and/or long oligonucleotides, and anchor oligos can have one or more variable nucleotides. Any one or more of the oligos can have 3 or 4 or 5 or 6 or 7 or 3-7 or 4-5 or 4-6 or 4-7 variable nucleotides in one or more regions or portions of the oligonucleotide sequence having variable nucleotides. The one or more variable nucleotides can be present as one consecutive sequence to comprise a variable region, or the variable nucleotides can be separated singly or in groups of two or more consecutive nucleotides throughout the oligo sequence to comprise a variable region. Oligonucleotides having variable nucleotides can represent a different sequence for each possibility presented by the variable nucleotides. For example, O1 can have a variable region. When the variable region is five nucleotides, O1 can have 1024 possible nucleotide sequences, i.e. 4×4×4×4×4 equals 1024 variable sequences for O1. The same is true for O2-O6 as depicted in FIG. 1a and for O1-O4 depicted in FIG. 1b, which show embodiments where any of the oligonucleotides can have one or more variable nucleotides in one or more regions of the oligo sequence. For short oligonucleotides each nucleotide of the oligo can be variable, i.e. the entire short oligo can be one variable region. But some short oligos can also have variable nucleotides dispersed in the sequence, singly or in groups as explained above. Each variable sequence of an oligo can be located at a distinct location in the oligo library.

Degenerate Nucleotides

One or more anchor strands used in the methods can, optionally, have one or more degenerate nucleotides. A degenerate nucleotide in an oligo of defined sequence is a nucleotide that can be any of A, C, T, or G. An oligo having degenerate nucleotides is a degenerate oligonucleotide. While similar to oligos having variable nucleotides, degenerate oligos are co-located at the same (degenerate oligonucleotide) location in an oligo library. Degenerate oligos can thus be present at a location as a group, with each degenerate oligo having a separate sequence due to the degenerate nucleotides. In some embodiments degenerate nucleotides on one oligo can anneal to a variable region on another oligo, such as is depicted in FIG. 1a-b. In various embodiments any of the oligonucleotides in a binding set can have degenerate nucleotides, and any of the oligonucleotide can have variable nucleotides. In some embodiments at least two oligonucleotides in a binding set have degenerate nucleotides. With reference to FIG. 1a O5 and O6 can have degenerate oligonucleotides, or O1 and O4, or O2 and O3, and not the other oligonucleotides in the binding set. With reference to FIG. 1b, O4 can have degenerate nucleotides, or O1 and O3 can have degenerate nucleotides, or O2 can have degenerate nucleotides, and not the other oligonucleotides in the binding set.

The one or more anchor strands can have 3 or 4 or 5 or 6 or 7 or 8 or 3-5 or 3-6 or 3-7 or 3-8 or 4-5 or 4-6 or 4-7 or 4-8 degenerate nucleotides. The one or more degenerate nucleotides in an oligo can be present as one consecutive sequence to comprise a degenerate region, or the degenerate nucleotides can be separated singly or in groups of two or more consecutive degenerate nucleotides throughout the oligo (e.g. an anchor strand). Oligonucleotide members of the library having degenerate nucleotides have multiple possible sequences and can be grouped together and located at a single location in the library, and be considered as one oligonucleotide member of the library. Thus, an anchor oligo (or other oligo) having a degenerate region of, for example, five degenerate nucleotides can have 1024 possible sequences (4×4×4×4×4), but all 1024 sequences can be co-located at a single defined location in the library. A location in the oligo library containing the multiple sequences of degenerate oligonucleotides is termed a degenerate oligonucleotide location. Multiple degenerate oligonucleotides (each of slightly different sequence) can be co-located at a single location in the oligo library. While in some embodiments all possible sequences of a degenerate oligonucleotide are located at the same location (e.g. all 1024 possible sequences of a degenerate oligo having 5 degenerate nucleotides), in other embodiments multiple degenerate oligonucleotides can be located in groups of convenient numbers at multiple different locations in the oligo library.

In addition to a degenerate sequence, anchor oligonucleotides can also have one or more variable nucleotides, which can be located in a variable region of the oligo. When an anchor (or other) oligo has variable nucleotides, for example five variable nucleotides, there are 1024 possible variable sequences (4×4×4×4×4) of the oligo. When oligos have one or more variable nucleotides each variable sequence of the oligo can be located at its own defined location in the library. Thus, while oligos having one or more degenerate nucleotides are co-located at a single defined location in the library, oligos having variable nucleotides can each have their own defined location in the library, a separate location for each possible variable sequence. An oligonucleotide such as an anchor strand having one or more degenerate nucleotides can be co-located at a single location having all 1024 possible sequences of the anchor strand having degenerate nucleotides present at the single location. When an oligonucleotide having variable nucleotides also has degenerate nucleotides, the degenerate sequences can also be present at all 1024 locations of the oligos having variable nucleotides, and each oligo at a defined location having the degenerate sequences can have the same variable sequence at that location.

For illustration, consider oligo O5 in FIG. 1a having a variable region of five nucleotides, and a degenerate region of five nucleotides. O5 can thus be present at variable locations L1 . . . L1024 for O5, with each location having each of degenerate sequences D1 . . . D1024 and a distinct variable sequence. Thus, degenerate sequences D1-D1024 can all be present at each of variable locations L1-L1024 for O5, each having a distinct variable sequence. Thus, at location L1 for O5 degenerate sequences D1-D1024 will all have variable sequence V1. At location L2 for O5, degenerate sequences D1-D1024 will all have variable sequence V2. At location L3 for O5 degenerate sequences D1-D1024 will all have variable sequence V3, and so on. Thus, degenerate sequences D1-D1024 for O5 are all present at locations L1-L1024 for O5, with each degenerate sequence having the variable sequence for the particular location. With respect to O1-O4 in FIG. 1a, these oligos have only variable regions and no degenerate nucleotides. Thus, if each has a variable region of five nucleotides, 1024 possible sequences exist for each oligo (4×4×4×4×4), which can be present at 1024 distinct locations in the library (L1 . . . L1024) for each oligo. Thus, a variable region on one oligo can anneal to a variable region and/or to a degenerate region on a complementary oligo.

Oligonucleotide Library

The invention also provides methods of synthesizing a product DNA molecule involving providing a library of oligonucleotide members. The library of oligonucleotide members can have fewer than 20,000 oligonucleotide members, and the oligonucleotide members in the library can be assembled into all possible polynucleotide sequences. The method involves assembling oligonucleotide members from the library to obtain the product DNA molecule.

With reference to FIG. 1a all oligonucleotides, O1-O6, are members in the library. O1, O2, O3, and O4 can each optionally have one or more variable regions. The oligonucleotide library can be one or more DNA chip, solid support, solid phase, bead, microfluidic surface, plate, etc, or other structure where oligonucleotides can be stored at defined locations and be available for retrieval and use in the methods. Thus, in some embodiments the library will contain a distinct location for each of the possible variable sequences of O1, O2, O3, and O4 (in embodiments where O1-O4 each have a variable region). When O1-O4 have a variable region having 5 variable nucleotides, the number of locations to accommodate the possible sequences of the oligos is 4 to the $5^{th}$ power ($4^5$), thus 4×4×4×4×4. Thus, in some embodiments there is a defined oligo sequence at 1024 defined locations, with a single or unique defined sequence present at each location. Thus, O1 oligos can have 1024 possible sequences, which can be present at 1024 defined locations for O1 with a single defined sequence at each location. Each oligo can have more or less than 5 variable nucleotides. It will thus be realized that any of the oligos can have a variable region and/or a degenerate region. In one embodiment only the anchor strands have both a variable region and a degenerate region.

Considering the embodiment of FIG. 1a as an example, with oligos O1-O6 having five variable nucleotides in a variable region, and five degenerate nucleotides in a degenerate region. In this embodiment O2 and O3 are short oligos, each comprised only of five variable nucleotides; O1 and O4 each have a variable region and will thus each have 1,024 locations. The library can thus have 1024 locations for each of O1-O4, i.e. 4,096 locations. O5 and O6 in this example each have five variable nucleotides, and five degenerate nucleotides. Thus, the library can also have 1,024 locations for each of O5 and O6, with each location having a distinct variable sequence, and all possible degenerate sequences, thus 1,024 degenerate oligo sequences are present together at each of the 1,024 locations for each variable sequence. This example thus gives a total of 6,144 distinct locations in the library.

Similarly, considering the embodiment of FIG. 1b, oligos O1-O4 can have five variable nucleotides in a variable region. O4 can further have five degenerate nucleotides in a degenerate region, where the degenerate nucleotides can all be co-located with each particular variable sequence. O2 is a short oligo comprised only of five variable nucleotides; O1 and O3 are long oligonucleotides and each have a variable region and will thus each have 1,024 locations. The library can thus have 1,024 locations for each of O1-O4, i.e. 4,096 distinct locations in the library. But in other embodiments only some of the oligonucleotides in a binding set can have variable nucleotides.

A location in the oligo library can be a well, a tube, or any other structure that segregates an oligonucleotide member in a distinct location, spatially separated from other members of the library sufficiently for it to be accessed individually and as a species at this distinct location. The oligos can be maintained in their distinct locations as a single molecule (from which a complementary sequence can be synthesized) or as a multiple copies of the same molecule (from which a small volume can be taken and used in synthesis procedures). Some oligonucleotide library members will have more than one actual sequence because of degenerate regions. The distinct locations can be identifiable to a software program that can be configured to a mechanical component or device that retrieves library members from the distinct location for use in a method where the defined oligonucleotide library member is required. In one embodiment an oligo library can be located in a collection of small tubes, each containing a member of the oligo library, and to which instrumentation components can go and retrieve an oligo library member according to instructions located on a non-transitory computer-readable medium. The non-transitory computer readable medium can also contain programmed instructions and/or steps for synthesizing a product DNA molecule, and the programmed instructions and/or steps can be provided to an instrument in communication with the computer-readable medium. The programmed instructions or steps can direct the instrumentation to perform the assembly of a DNA molecule of pre-defined sequence according to any method disclosed herein, or to perform any of the methods provided herein.

Members of the oligonucleotide library are present at distinct locations, spatially separated from other members of the library. A member of the library can be a specific sequence present at its location (either singly or multiple copies). But a member can also be a group of similar sequences present at a distinct or defined location. When degenerate sequences are used, the member of the library containing degenerate sequences can be all possible degenerate sequences (or in some embodiments a subset of all possible sequence) in view of the number of degenerate nucleotides, and present at a distinct location. For example, for an oligonucleotide member having a region of 5 degenerate nucleotides, that member can comprise 4×4×4×4×4 or 1024 distinct oligonucleotides, which can be co-located at a distinct location in the library. Thus, the oligonucleotide library can have fewer than 20,000 distinct locations, with a member of the library being present at the fewer than 20,000 distinct locations. In some embodiments there can be a number of sequences of the all possible sequences that are not of interest. Thus, only a subset of all possible degenerate sequences need be present at the distinct location. Thus, in some embodiments a subset of all possible degenerate sequences can be present as a member of the oligonucleotide library at a distinct location. A distinct location in the oligo library is an identifiable position to which instrumentation can go to obtain the oligonucleotide member at that location. In any embodiment the distinct location can be defined by any suitable technique, for example reference points in a microscopic picture or grid of the solid support containing the oligo library. In some embodiment the distinct location can be stored on and/or communicated by a non-transitory computer-readable medium.

Product DNA with Overhangs

After removal of flanking sequences (when used), the product DNA molecules can be assembled if desired. In some embodiments the product DNA molecules will be double-stranded blunt end DNA. DNA molecules can be synthesized so that they each contain an overlap or "sticky end" (e.g. one-half the length of the oligo), which can then be used to assemble them into a larger DNA molecule.

But in other embodiments the product DNA molecule can be synthesized having single-stranded overhangs of one or more bases. Type IIS restriction enzymes cleave DNA at a defined distance from their recognition site. As a result Type IIS restriction endonucleases find application in the invention for producing product DNA molecules having single-stranded overhangs. These product DNA molecules can then be joined by annealing to a product DNA molecule having a complementary overhanging sequence to form a larger DNA molecule.

Figure 5:
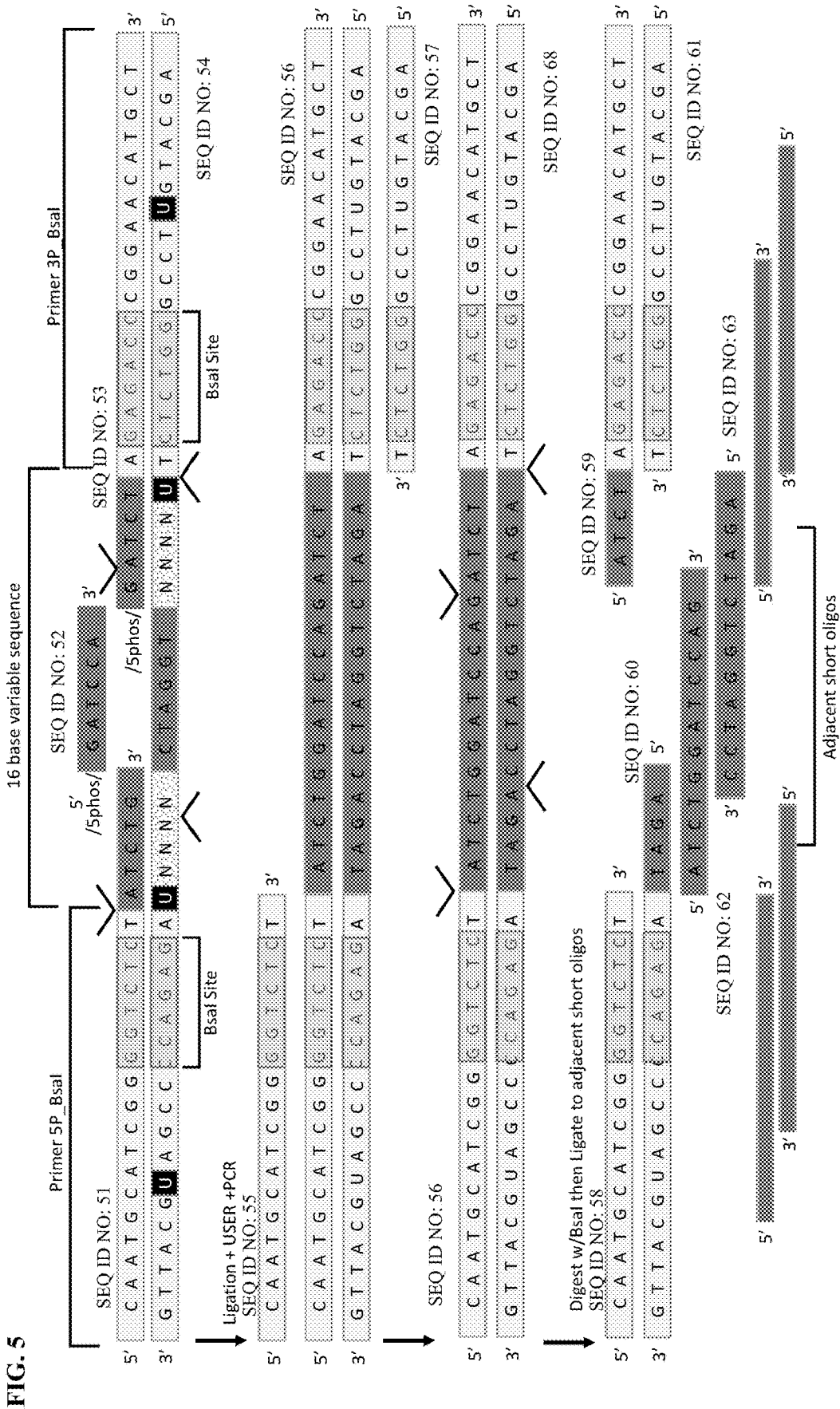
FIG. 5 provides a schematic illustration of the use of restriction endonucleases in the invention to generate product DNA molecules having "sticky" ends. The restriction enzymes cut a defined number of nucleotides away from the recognition site.

In any embodiment the methods can further involve a step of contacting the product DNA molecule with a Type IIS restriction endonuclease to generate a product DNA molecule having single-stranded overhangs. In any embodiment the methods can also involve a step of joining together two or more of the resultant product DNA molecules to produce a longer product DNA molecule. As shown in FIG. 5, recognition sites can be encoded into flanking sequences to enable the release of a double-stranded product DNA molecule having single-stranded overhangs (i.e. "sticky" ends). The single-stranded overhangs can be any suitable length, for example 4 or 5 or 6 or 7 or 8 or more than 8 nucleotides or 6-10 nucleotides or 7-9 nucleotides. In one embodiment the single-stranded overhangs can be one-half the length of the product DNA molecule, or 1 or 2 bases more or less than one-half the length of the product DNA. For example if the length of the product DNA molecule is 16 nucleotides the overhang can be 8 nucleotides or 6-10 nucleotides. In one embodiment BsaI sites can be encoded into the flanking sequences, as depicted in FIG. 5. BsaI recognizes the sequence 5'-GGTCTC(N1)-3' (SEQ ID NO: 49). The enzyme generally cleaves to the 3' side of N. Another example of a useful Type IIS restriction enzyme is BsmBI, which recognizes the sequence 5'-CGTCTCN-3' (SEQ ID NO: 50), and generally cleaves to the 3' side of N. Persons of ordinary skill with resort to this disclosure will realize other restriction enzymes that will find use in the invention. Such persons can also easily determine where the enzymes will cut in any particular application. In any embodiment of the methods disclosed herein the DNA molecules produced by the methods can contain one or more Type IIS restriction endonuclease cleavage sites.

DNA Data Storage

Figure 6:
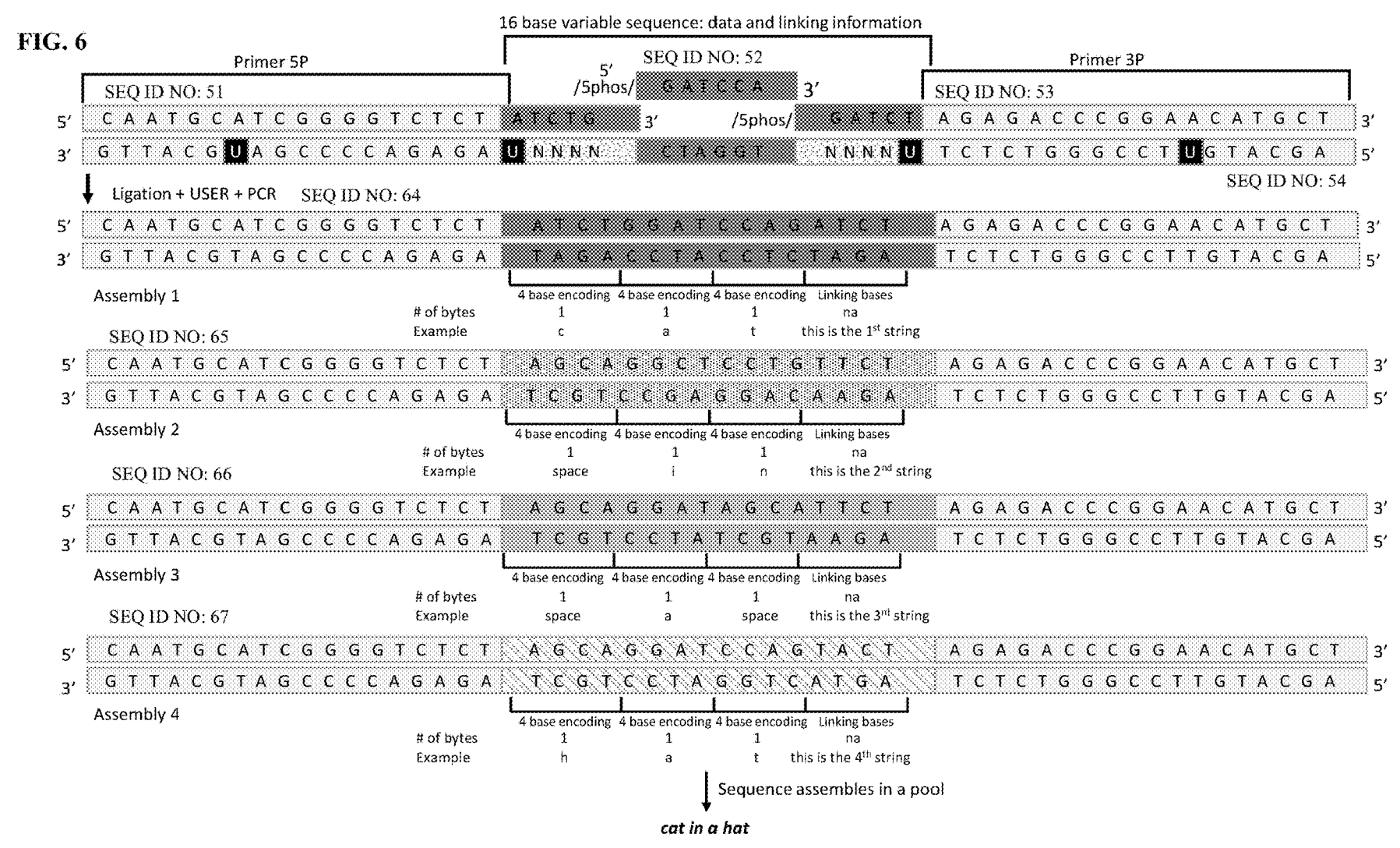

DNA is stable even over periods of thousands of years and even in many extreme environments, giving it great advantages for storing information. Any of the methods disclosed herein can also be applied to encoding digital data into DNA. One or more product DNA molecule(s) can have a sequence that comprises an encoded non-genetic message. One or more product DNA molecule(s) can have a sequence that corresponds to bytes of information that encode the non-genetic message. The bytes of information can be decoded with reference to a key that assigns one or more language character(s) to each encoded character or byte of information. For example, as illustrated in FIG. 6, a 16 bp product DNA molecule can be synthesized and easily accommodates four bytes of information, where each byte is encoded by an assigned sequence of nucleotides. In this example a four nucleotide sequence represents a byte of information, which can correspond to a character (e.g. a letter or numeral). Thus, in this example 256 characters can be encoded in each byte of information (4×4×4×4). Thus, the alphabet of any language in the world can be easily accommodated within these 256 bytes of information and a sufficient number of numerals and other characters utilized in communication as well.

The product DNA can also encode a character (e.g. a letter, a word, a number, a punctuation mark, word character, or other characters utilized in communication) indicating where in the sequence the information encoded by that DNA molecule is to be placed. FIG. 6 depicts 16 bp product DNA molecules having four bytes of four nucleotides each. The last byte in each product DNA sequence indicates the location in the message where the preceding three bytes are placed; this is conveniently a numeral but can be any character that can be placed into a definable sequence. While a 4 nucleotide byte provides up to 256 identifiers the byte can be any convenient length of nucleotides. For example, bytes can be comprised of 5 nucleotides or 6 nucleotides (allowing for 4,096 identifiers), or 7 or even 8 nucleotides, or more than 8 nucleotides, allowing for many more identifiers to be included. Limited numbers of identifiers can also be expanded by placing DNA molecules in a single well up to the number of identifiers, and then assembling the messages from the DNA in the order of the sequence of wells. Using this method with only a 4 nucleotide identifier even a single 384 well plate can contain over 98,000 DNA molecules (256 molecules×384 wells), which can be assembled in order to provide almost 300,000 bytes of information (in addition to the identifier). When a 5 nucleotide identifier is used over 1,024 molecules can be individually identified times 384 wells, i.e. 393,000 molecules, or over 1 million bytes of information in a single plate. Multiple plates can be used to accommodate much greater amounts of information. Therefore, an unlimited amount of information can be encoded and stored indefinitely according to the methods.

CRISPR Guide RNA

Figure 7:
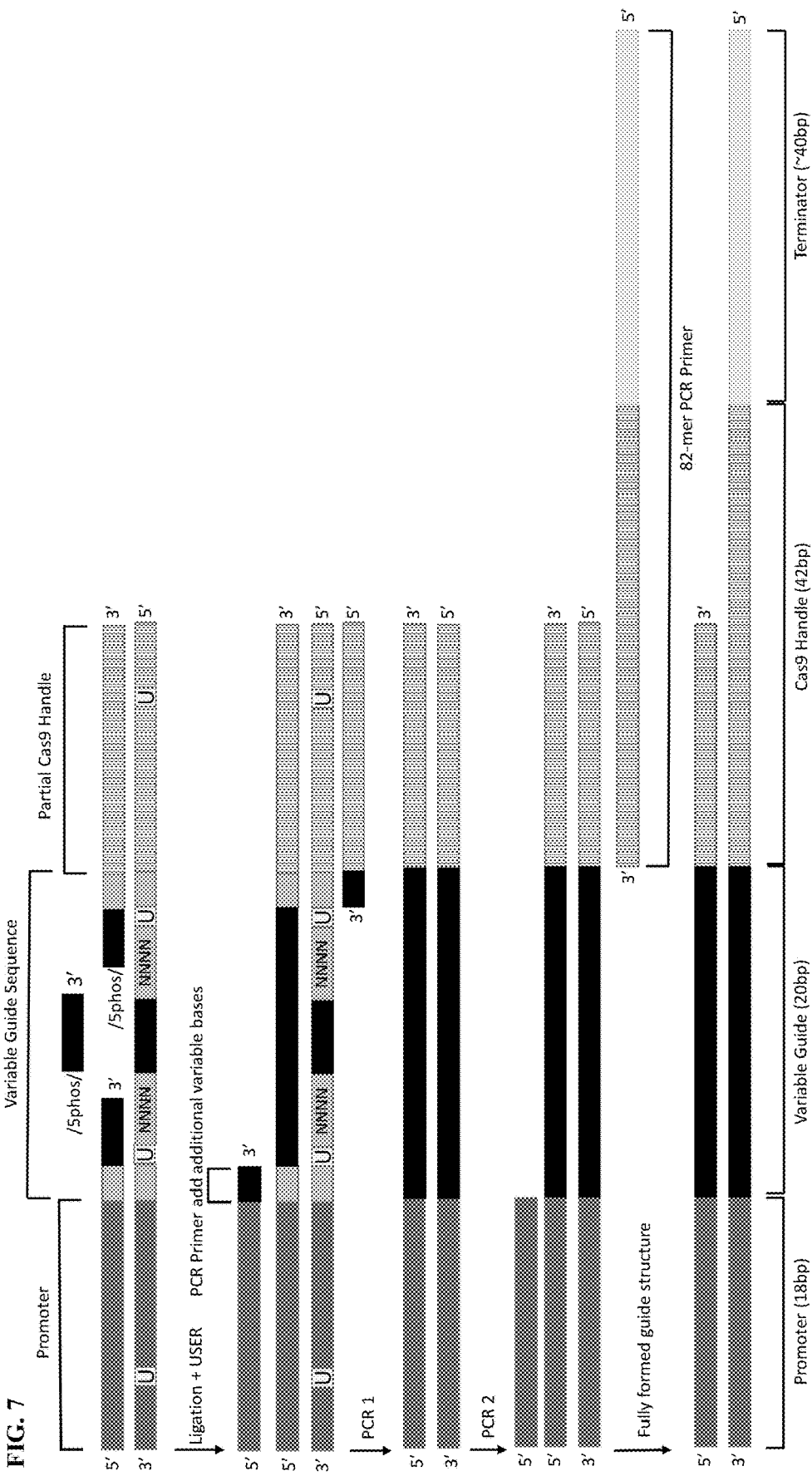
FIG. 7 is a schematic illustration of an embodiment of the invention applied to synthesizing a 120 bp product DNA, which is an initial guide structure having the transcriptional elements of a promoter, a guide RNA, a Cas9 handle, and a terminator. In this embodiment the first cycle of PCR utilizes two primers having two variable bases on their 3' ends. This converts the otherwise 16 bp product DNA molecule into a 20 bp product. Later step(s) of PCR incorporate transcriptional elements.

The invention can also be applied to the synthesis of guide RNAs (gRNA) for use in CRISPR-Cas9 methods. Using the methods any sequence of gRNA can be quickly constructed. Guide RNA constructs can also be constructed from oligonucleotides in the oligonucleotide library. A product DNA molecule can be synthesized in the methods having a DNA sequence of an initial guide structure. The initial guide RNA structure can encode a gRNA with the necessary prokaryotic or eukaryotic transcriptional elements for in vitro transcription in proper order, for example any one or more of a promoter, a sequence of gRNA, and a terminator. In some embodiments the gRNA can encode a Cas9-binding hairpin (Cas9 handle). In some embodiment the transcriptional elements include a promoter and/or a terminator. In some embodiments the product DNA molecule can encode 20 bases for the gRNA. FIG. 7 depicts one embodiment in which short and long oligos of the invention (which can be from an oligo library) are synthesized in the methods into an initial guide structure having the transcriptional elements. Any embodiment of the methods disclosed herein can be used to synthesize the guide structure. Since all possible polynucleotide sequences can be assembled from the oligo library, any initial guide structure can be assembled in the methods. As explained herein product DNA molecules can be synthesized so that they can be ligated to synthesize larger DNA molecules.

Adding Bases

In any embodiment the methods can include a step that can add 2 or 3 or 4 or 5 or 6 or 7 or 8 or 2-4 or 2-6 or 2-8 or 2-10 or 2-12 extra nucleotides to the product DNA molecule. In the embodiment depicted in FIG. 7 a 16 bp product DNA molecule is synthesized by annealing of the short oligonucleotide(s), long oligonucleotides, and anchor strand(s), according to any of the methods disclosed herein. The long and/or short oligos and anchor strand(s) can be made to provide extra nucleotides (e.g. two or more extra nucleotides) that will become part of the product DNA molecule after an amplification step. Any embodiment of the methods can involve multiple steps of PCR or other DNA amplification technique. In any embodiment during a step of PCR primers can be used where the non-standard nucleotides (e.g. dU) are recessed or set back by one or more, or two or more nucleotides from the 3' end of the primers, or set back by 2 or 3 or 4 or 5 or 6 or 7 or 8 or 2-4 or 2-6 or 2-8 or 2-10 or 2-12 nucleotides. This allows for amplification of the extra nucleotide(s) on each side of the product DNA molecule and their inclusion in the product DNA molecule. In some embodiments this is done during a first or early step of PCR. The result is a product DNA molecule that has been extended by, for example, two extra nucleotides on each side. Thus, a 16 bp product DNA molecule can be extended in the method to a 20 bp product DNA molecule.

EMBODIMENTS

Various lengths of long oligonucleotides, short oligonucleotides, and anchor strands can be used in the methods disclosed herein, whether in the embodiment depicted in FIG. 1a or the embodiment depicted in FIG. 1b. Various sizes of long oligonucleotides, short oligonucleotides, and anchor strands can be used in the methods, and in all possible combinations and sub-combinations.

In some embodiments the at least one long oligonucleotide is from 12-24 nucleotides in length, the at least one short oligonucleotide is 4-8 nucleotides in length, and the at least one anchor strand is from 20-60 nucleotides in length; or the at least one long oligonucleotide is from 12-24 nucleotides in length, the at least one short oligonucleotide is 4-8 nucleotides in length, and the at least one anchor strand is from 12-60 nucleotides in length; or the at least one long oligonucleotide is from 12-24 nucleotides in length, the at least one short oligonucleotide is 4-8 nucleotides in length, and the at least one anchor strand is from 12-80 nucleotides in length. In one embodiment the at least one long oligonucleotide is from 12-24 nucleotides in length, the at least one short oligonucleotide is 4-10 nucleotides in length, and the at least one anchor strand is from 20-60 nucleotides in length; or the at least one long oligonucleotide is from 12-24 nucleotides in length, the at least one short oligonucleotide is 4-10 nucleotides in length, and the at least one anchor strand is from 12-60 nucleotides in length; or the at least one long oligonucleotide is from 12-24 nucleotides in length, the at least one short oligonucleotide is 4-10 nucleotides in length, and the at least one anchor strand is from 12-80 nucleotides in length. In one embodiment the at least one long oligonucleotide is from 12-24 nucleotides in length, the at least one short oligonucleotide is 4-12 nucleotides in length, and the at least one anchor strand is from 20-60 nucleotides in length; or the at least one long oligonucleotide is from 12-24 nucleotides in length, the at least one short oligonucleotide is 4-12 nucleotides in length, and the at least one anchor strand is from 12-60 nucleotides in length; or the at least one long oligonucleotide is from 12-24 nucleotides in length, the at least one short oligonucleotide is 4-12 nucleotides in length, and the at least one anchor strand is from 12-80 nucleotides in length.

In some embodiments the at least one long oligonucleotide is from 12-30 nucleotides in length, and the at least one short oligonucleotide is from 4-8 nucleotides in length, and the at least one anchor strand is from 20-60 nucleotides in length; or the at least one long oligonucleotide is from 12-30 nucleotides in length, and the at least one short oligonucleotide is from either of 4-8 nucleotides in length, and the at least one anchor strand is from 12-60 nucleotides in length; or the at least one long oligonucleotide is from 12-30 nucleotides in length, and the at least one short oligonucleotide is from either of 4-8 nucleotides in length, and the at least one anchor strand is from 12-80 nucleotides in length. In another embodiment the at least one long oligonucleotide is from 12-30 nucleotides in length, and the at least one short oligonucleotide is from 4-10 nucleotides in length, and the at least one anchor strand is from 20-60 nucleotides in length; or the at least one long oligonucleotide is from 12-30 nucleotides in length, and the at least one short oligonucleotide is from either of 4-10 nucleotides in length, and the at least one anchor strand is from 12-60 nucleotides in length; or the at least one long oligonucleotide is from 12-30 nucleotides in length, and the at least one short oligonucleotide is from either of 4-10 nucleotides in length, and the at least one anchor strand is from 12-80 nucleotides in length. In another embodiment the at least one long oligonucleotide is from 12-30 nucleotides in length, and the at least one short oligonucleotide is from 4-12 nucleotides in length, and the at least one anchor strand is from 20-60 nucleotides in length; or the at least one long oligonucleotide is from 12-30 nucleotides in length, and the at least one short oligonucleotide is from either of 4-12 nucleotides in length, and the at least one anchor strand is from 12-60 nucleotides in length; or the at least one long oligonucleotide is from 12-30 nucleotides in length, and the at least one short oligonucleotide is from either of 4-12 nucleotides in length, and the at least one anchor strand is from 12-80 nucleotides in length.

In some embodiments the at least one long oligonucleotide is from 12-40 nucleotides in length, and the at least one short oligonucleotide is from either of 4-8 nucleotides in length, and the at least one anchor strand is from 20-60 nucleotides in length. In another embodiment the at least one long oligonucleotide is from 12-40 nucleotides in length, and the at least one short oligonucleotide is from either of 4-8 nucleotides in length, and the at least one anchor strand is from 12-60 nucleotides in length. In another embodiment the at least one long oligonucleotide is from 12-40 nucleotides in length, and the at least one short oligonucleotide is from either of 4-8 nucleotides in length, and the at least one anchor strand is from 12-80 nucleotides in length. In another embodiment the at least one long oligonucleotide is from 12-40 nucleotides in length, and the at least one short oligonucleotide is from either of 4-10 nucleotides in length, and the at least one anchor strand is from 20-60 nucleotides in length. In another embodiment the at least one long oligonucleotide is from 12-40 nucleotides in length, and the at least one short oligonucleotide is from either of 4-10 nucleotides in length, and the at least one anchor strand is from 12-60 nucleotides in length. In another embodiment the at least one long oligonucleotide is from 12-40 nucleotides in length, and the at least one short oligonucleotide is from either of 4-10 nucleotides in length, and the at least one anchor strand is from 12-80 nucleotides in length. In another embodiment the at least one long oligonucleotide is from 12-40 nucleotides in length, and the at least one short oligonucleotide is from either of 4-12 nucleotides in length, and the at least one anchor strand is from 20-60 nucleotides in length. In another embodiment the at least one long oligonucleotide is from 12-40 nucleotides in length, and the at least one short oligonucleotide is from either of 4-12 nucleotides in length, and the at least one anchor strand is from 12-60 nucleotides in length. In another embodiment the at least one long oligonucleotide is from 12-40 nucleotides in length, and the at least one short oligonucleotide is from either of 4-12 nucleotides in length, and the at least one anchor strand is from 12-80 nucleotides in length.

Furthermore, in any of the embodiments annealing of nucleic acids can begin with denaturation, which can be performed at a temperature of 90° C. or higher, or 95° C. or higher, or 98° C. or higher. Similarly, annealing can occur at temperatures of 35° C. or lower, or 30° C. or lower, or 25° C. or lower. In one embodiment denaturation occurs at 98° C. or higher, and annealing occurs at 25° C. or lower. In another embodiment denaturation occurs at 96° C. or higher, and annealing occurs at 27° C. or lower. The methods can involve transitioning from the denaturation temperature to the annealing temperature at a rate of 1° C./s or at a rate of 0.1° C./s. In one embodiment the transition can go from the denaturation temperature to about 85° C. at a rate of 1° C./s, and then go from about 85° C. to the annealing temperature at a rate of 0.1° C./s. Annealing and denaturation can be performed in cycles and can be performed in a cycle repeated at least 20 times or at least 25 times or at least 30 times or about 30 times.

Persons of ordinary skill with resort to this disclosure know conditions under which ligation of abutting long and short oligonucleotides can occur while they are bound to the anchor strand(s), which conditions can be readily determined. In various embodiments ligation can occur different temperatures to allow for full settling and annealing of oligonucleotides and anchor strands, and a method can be used to allow for maximal annealing. In various embodiments ligation can occur at for about 5-15 seconds or 8-12 seconds or about 10 seconds at 37° C.±2° C., then about 5-15 seconds or 8-12 seconds or about 10 seconds at 16° C.±2° C., then about 5-15 seconds or 8-12 seconds or about 10 seconds at 4° C.±2° C. In other embodiments ligation can occur at for about 5-15 seconds or 8-12 seconds or about 10 seconds at 37° C.±1° C., then about 5-15 seconds or 8-12 seconds or about 10 seconds at 16° C.±1° C., then about 5-15 seconds or 8-12 seconds or about 10 seconds at 4° C.±1° C.

Persons of ordinary skill with resort to this disclosure also know conditions under which anchor strands containing non-standard nucleotides can be depleted. Conditions can be based on conditions for depleting primers. In various embodiments the conditions can be 35-45° C. for 45-75 minutes, or about 37° C. for 60 minutes followed by 65° C. for 10 minutes.

Example 1

This example illustrates synthesis of four different 20mers of varying GC content using an embodiment of the method depicted in FIG. 1a. The product DNA molecules (SEQ ID NOs: 1-4) were synthesized with 18 bp flanking sequences. These sequences are provided for illustration and any sequence can be assembled using the methods.

The same procedures were followed for the synthesis of each of SEQ ID NOs: 1-4. For synthesis of SEQ ID NO: 1, mixtures 1 and 2 were formed. Mixture 1 contained restriction enzyme buffer (50 mM potassium acetate, 20 mM Tris-acetate, 10 mM magnesium acetate, and 100 ug/ml BSA, at pH 7.9, commercially available as CutSmart® buffer, New England Biolabs, Inc., Ipswich, MA) to simplify double digest reactions, 100 uM each of O2 (SEQ ID NO: 10), O3 (SEQ ID NO: 11), O5 (SEQ ID NO: 13), and O6 (SEQ ID NO: 14), and water. Mixture 2 contained the same restriction enzyme buffer, 100 uM of O1 (SEQ ID NO: 9) and O4 (SEQ ID NO: 12), and water. The oligonucleotides were as follows:
  O1, O4 (long oligos): 18 nt (universal flank)+4-6 nt variable region
  O2, O3 (short oligos): 4-6 nt variable region
  O5, O6 (anchor strands): 18 nt universal flank+3-5 nt of degenerate bases+4-6 nt variable region.

Mixtures 1 and 2 were combined and subjected to denaturation and annealing conditions as follows:
  98° C. —2 min
  ramp down to 85° C. at 1° C./s.
  85° C. —2 min.
  ramp down to 25° C. at 0.1° C./s
  25° C. —2 min.

After denaturation and annealing the mixture was subjected to the ligation reaction, which was conducted with T4 ligase under a ligation protocol, which included 30 cycles of:
  37° C. —10 s
  16° C. —10 s
  4° C. —10 s The same cycles were then repeated 30 more times to end with 70° C. for 15 min in preparation for anchor strand depletion.

The mixture was then subjected to an anchor strand depletion step using uracil DNA glycosylase (UDG) and DNA glycosylase-lyase endonuclease VIII for uracil-specific excision that generates a single nucleotide gap at the location of a uracil residue. The reaction conditions were 37° C. for 60 minutes followed by 65° C. for 10 minutes.

The anchor strand depletion mixture was diluted 1:100 and 2 ul was used as a template in the final PCR amplification reaction. The PCR reaction components included the DNA polymerase (VeraSeq® 2.0 high-fidelity DNA polymerase (Qiagen Beverly, LLC, Beverly, MA,), universal primers, dNTPs, and template. The PCR protocol was as follows:
  98° C. —30 s
  30 cycles of
    98° C. —10 s
    60° C. —10 s
    72° C. —15 s
  72° C. —10 min As show in FIG. 3, all four product DNA molecules of 20 bp and of varied GC content were assembled with 18 bp flanking sequences to produce 56 bp amplicons, which were resolved on a 4% agarose gel. SEQ ID NO: 1-4 were confirmed by Sanger sequencing of 24 clones and found to have the expected sequence.

Synthesis of SEQ ID NOs: 2-4 was the same, using the following oligonucleotides from the oligo library.
  For SEQ ID NO: 2-O1 (SEQ ID NO: 15), O2 (SEQ ID NO: 16), O3 (SEQ ID NO: 17), O4 (SEQ ID NO: 18), O5 (SEQ ID NO: 19), O6 (SEQ ID NO: 20).
  For SEQ ID NO: 3-O1 (SEQ ID NO: 21), O2 (SEQ ID NO: 22), O3 (SEQ ID NO: 23), O4 (SEQ ID NO: 24), O5 (SEQ ID NO: 25), O6 (SEQ ID NO: 26).
  For SEQ ID NO: 4-O1 (SEQ ID NO: 27), O2 (SEQ ID NO: 28), O3 (SEQ ID NO: 29), O4 (SEQ ID NO: 30), O5 (SEQ ID NO: 31), O6 (SEQ ID NO: 32).

Figure 3:
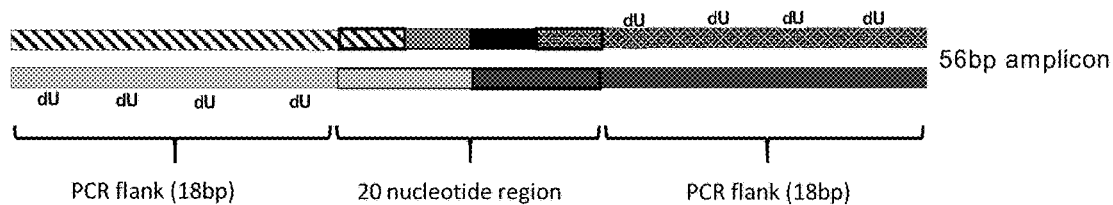
FIG. 3 is a schematic illustration of the assembly of product DNA molecules of varying GC content. Four oligonucleotide sequences (SEQ ID NOs: 1-4) with a GC range of 30-60% were assembled according to the procedure of Example 1 and FIG. 1a. 20 bp DNA products were assembled having 18 bp flanking sequences. dU are depicted as part of the oligonucleotide sequence.
Figure 3:
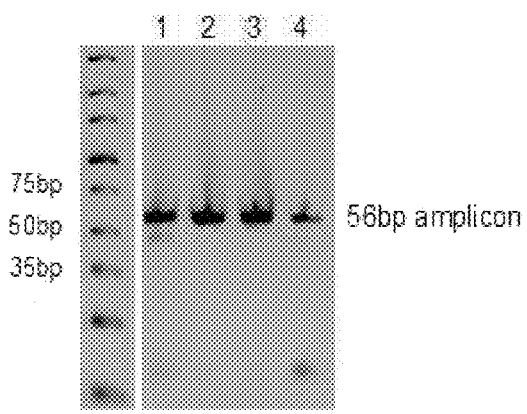

As illustrated in FIG. 3 and confirmed by Sanger sequencing, all sequences were shown to have the correct and defined sequence.

Example 2

This example shows another embodiment illustrating synthesis of four product DNA molecules (SEQ ID NOs: 5-8) where the binding sets contained two long oligonucleotides, one short oligonucleotide, and one anchor strand, an embodiment of which is depicted in FIG. 1b. The 20 bp product DNA molecules were synthesized with 18 bp flanking sequences, providing a final amplicon length of 56 bp.

Figure 4:
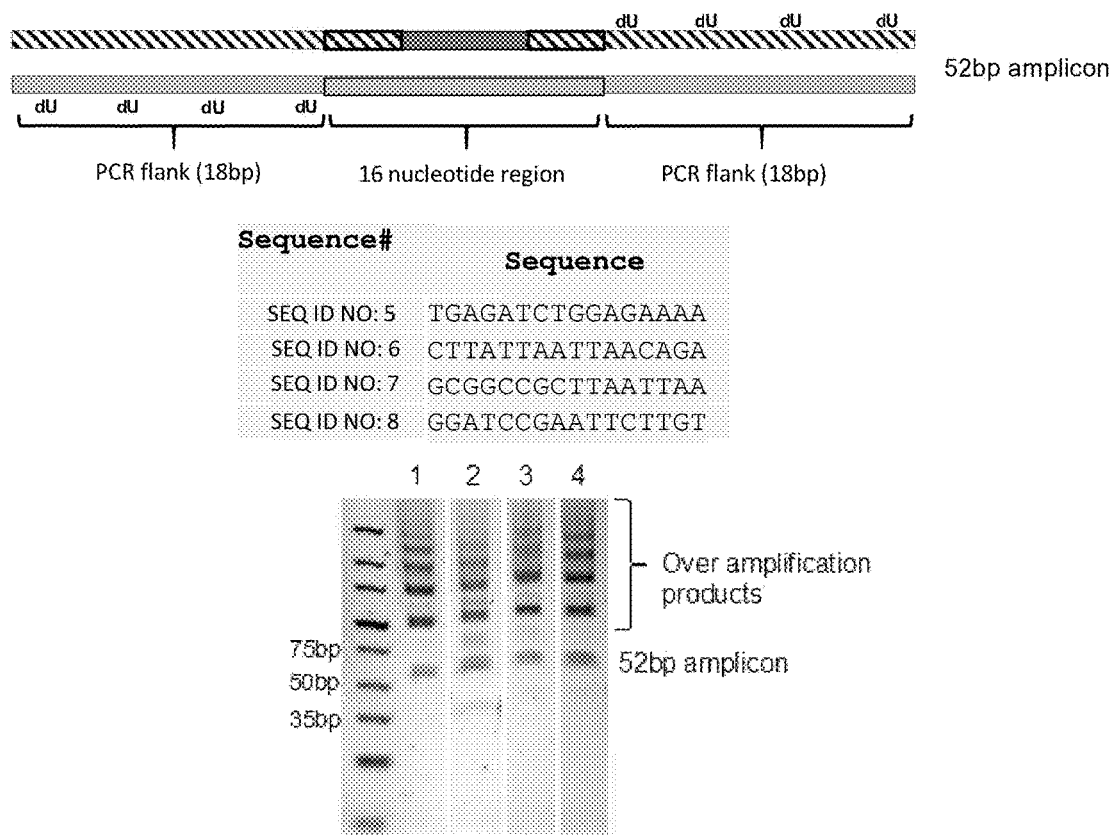
FIG. 4 is a schematic illustration of the assembly of product DNA molecules of varying GC content. Four oligonucleotides sequences (SEQ ID NOs: 5-8) with a GC range of 30-60% were assembled according to the procedure of Example 2 and FIG. 1b. 16 bp DNA products were assembled having 18 bp flanking sequences. dU are depicted as part of the oligonucleotide sequence.

The same procedures were followed for the synthesis of each of SEQ ID NOs: 5-8. For synthesis of SEQ ID NO: 5, mixtures O1 (SEQ ID NO: 33), O2 (SEQ ID NO: 34), O3 (SEQ ID NO: 35) and O4 (SEQ ID NO: 36) were contained in a mixture. O1 and O3 are long oligonucleotides, O2 is a short oligonucleotide, and O4 is the anchor strand. The oligonucleotides were as follows:
  O1, O3 (long oligos): 18 nt universal flanks+4-6 nt variable region
  O2 (short oligo): 6 nt variable region
  O4 (anchor strand): 52 nt Protocols were the same as those in Example 1. The result is shown in FIG. 4, which shows an agarose gel with the four amplicons resolved. The four 16 bp DNA products (SEQ ID NOs: 5-8) were successfully assembled with their 18 bp flanking sequences to result in 52 bp amplicons. Assembly was demonstrated on a 4% agarose gel (FIG. 3). The sequences of the final products were confirmed by Sanger sequencing and found to be the expected sequences.

Synthesis of SEQ ID NOs: 6-8 were performed in the same manner, using the following oligonucleotides from the oligo library.

For SEQ ID NO: 6-O1 (SEQ ID NO: 37), O2 (SEQ ID NO: 38), O3 (SEQ ID NO: 39), O4 (SEQ ID NO: 40);

For SEQ ID NO: 7-O1 (SEQ ID NO: 41), O2 (SEQ ID NO: 42), O3 (SEQ ID NO: 43), O4 (SEQ ID NO: 44);

For SEQ ID NO: 8-O1 (SEQ ID NO: 45), O2 (SEQ ID NO: 46), O3 (SEQ ID NO: 47), O4 (SEQ ID NO: 48);

As illustrated in FIG. 4 (and confirmed by Sanger sequencing), all sequences were shown to have the correct and defined sequence.

What is claimed is:

1. A method of synthesizing a product DNA molecule having a desired and pre-determined sequence comprising:
   annealing at least one long oligonucleotide and at least one short oligonucleotide to at least one anchor strand(s) having a sequence at least partially complementary to the at least one long and at least one short oligonucleotide, wherein,
   (a) the annealing occurs within a binding set comprising at least two long oligonucleotides O1 and O4 of 9-35 nucleotides in length, two short oligonucleotides O2 and O3 of 5-7 nucleotides in length, and at least two anchor strands O5 and O6, wherein after annealing O1 abuts O2, and O3 abuts O4, and O1 and O2 are bound to the same anchor strand O5, and O3 and O4 are bound to the same anchor strand O6, to form double-stranded DNA molecules O1-O2-O5 and O3-O4-O6;
   ligating the abutting O1 and O2, and the abutting O3 and O4 to form double-stranded DNA molecules O1-O2-O5 and O3-O4-O6; and
   ligating double-stranded DNA molecules O1-O2-O5 and O3-O4-O6 by blunt end ligation to form a double-stranded DNA molecule; or
   (b) the annealing occurs within a binding set comprising at least two long oligonucleotides O1 and O3 of 9-35 nucleotides in length, one short oligonucleotide O2 of 5-7 nucleotides in length, and at least one anchor strand O4, wherein after annealing O2 abuts O1 and O3, and O1-O3 are bound to the same anchor strand O4 to form a double-stranded DNA molecule O1-O4;
   ligating the abutting O1 and O2, and the abutting O2 and O3 to form a double-stranded DNA molecule;
   wherein the anchor strand(s) each comprise one or more non-standard nucleotides,
   contacting the double-stranded DNA molecule with one or more enzymes that degrade DNA comprising one or more non-standard nucleotides to form a single-stranded DNA molecule;
   performing a step of amplification to produce an amplified double-stranded DNA molecule; and
   contacting the amplified double-stranded DNA molecule with a Type IIS restriction endonuclease to thereby synthesize the product DNA molecule having the desired and pre-determined sequence;
   and wherein the method is performed without any of the oligonucleotides being bound to a solid phase.

2. The method of claim 1 wherein the long and short oligonucleotides further comprise variable nucleotides, and the anchor strand(s) further comprise degenerate oligonucleotides.

3. The method of claim 2 wherein in step a) each anchor strand comprises 5-7 variable and/or 5-7 degenerate nucleotides comprised in a single degenerate region.

4. The method of claim 3 wherein the at least two long oligonucleotides further comprise variable nucleotides that bind to the degenerate nucleotides on their respective at least partially complementary anchor strand(s) during the annealing step, and wherein the long oligonucleotides, short oligonucleotides, and anchor strands are selected from an oligonucleotide library.

5. The method of claim 4 wherein the long oligonucleotides, short oligonucleotides, and anchor strand each comprise six variable nucleotides.

6. The method of claim 2 wherein in step b) the anchor strand comprises 4-6 variable and/or 4-6 degenerate nucleotides comprised in each of two degenerate regions.

7. The method of claim 2 wherein the long and short oligonucleotides each comprise 5-7 variable nucleotides.

8. The method of claim 2 wherein
   a. the short and long oligos comprise six variable nucleotides;
   b. the anchor strands comprise six degenerate nucleotides; and
   c. the anchor strand comprises at least two deoxy-uracil monophosphate nucleotides; and
   the product DNA molecule is amplified by PCR.

9. The method of claim 1 wherein the non-standard nucleotide is deoxy-uridine.

10. The method of claim 1 wherein the dsDNA molecule comprises the non-standard nucleotides on only one strand.

11. The method of claim 1 wherein the step of amplification comprises performing multiple cycles of PCR on the product DNA molecule.

12. The method of claim 11 wherein the product DNA molecule comprises flanking sequences for annealing a primer used in the multiple cycles of PCR.

13. The method of claim 12 wherein the product DNA molecule is 8-30 nucleotides in length, not including the flanking sequences.

14. The method of claim 12 wherein the product DNA molecule is 16-20 oligonucleotide in length.

15. The method of claim 12 wherein the product DNA molecule encodes a guide RNA, and the flanking sequences encode one or more transcriptional elements, and the guide RNA optionally encodes a Cas9-binding hairpin.

16. The method of claim 15 wherein the transcriptional elements comprise a promoter and a terminator.

17. The method of claim 11 wherein the multiple cycles of PCR comprise a first step of PCR using primers comprising non-standard nucleotides set two nucleotides back from the 3' end of the primer.

18. The method of claim 1 wherein the product DNA molecule is 8-30 nucleotides in length.

19. The method of claim 1 wherein the ligation is performed by a DNA ligase.

20. The method of claim 1 wherein the at least one long oligonucleotide is from 12-24 nucleotides in length, and the at least one short oligonucleotide is six nucleotides in length.

21. The method of claim 20 wherein the at least one anchor strand is from 20-60 nucleotides in length.

22. The method of claim 1 wherein the one or more enzymes that degrade DNA comprising non-standard nucleotides comprise one or more enzymes selected from the group consisting of: uracil DNA glycosylase, Endonuclease VIII, and Exonuclease T.

23. The method of claim 1 wherein the long and short oligonucleotides each comprise 5-7 variable nucleotides.

24. The method of claim 1 wherein the long oligonucleotide(s) and short oligonucleotide(s) are provided from an oligonucleotide library.

25. The method of claim 24 wherein the short oligonucleotide(s) provided from the oligonucleotide library is/are 5-6 nucleotides in length.

26. The method of claim 25 wherein the oligonucleotide library comprises long oligonucleotide members having all four possible nucleotides at each position of a variable nucleotide present at distinct locations.

27. The method of claim 26 wherein the long oligonucleotides comprise a variable region that anneals to the sequence of degenerate nucleotides on the one or more anchor strands.

28. The method of claim 1 wherein
   a. the short and long oligos comprise six variable nucleotides;
   b. the anchor strand comprises six degenerate nucleotides and at least two deoxy-uracil monophosphate nucleotides; and
   c. the product DNA molecule is amplified by PCR.

29. The method of claim 1 wherein the product DNA molecule has an error rate of fewer than 1 in 25,000.

30. The method of claim 1 wherein the at least one long oligonucleotide, at least one short oligonucleotide, and at least one anchor strand are selected from an oligonucleotide library comprising less than 20,000 members.

31. The method of claim 1 wherein the oligonucleotide library comprising less than 20,000 members contains oligonucleotides sufficient to synthesize all possible nucleotide sequences.

32. The method of claim 1 wherein in the Type IIS restriction endonuclease is BsaI or BsmBI.

33. The method of claim 1 wherein the product DNA molecule comprises an encoded non-genetic message.

34. The method of claim 33 wherein the product DNA molecule comprises a sequence corresponding to bytes of information, where each byte is encoded by an assigned sequence of nucleotides.

35. The method of claim 1 wherein the product DNA molecule is scarless DNA.

36. The method of claim 1 wherein the at least one anchor strand is selected from a location in an oligonucleotide library comprising degenerate oligonucleotides.

37. The method of claim 1 wherein the at least one long oligonucleotide and the at least one short oligonucleotide have a sequence that is fully complementary to the at least one anchor strand.

* * * * *

SEQUENCE LISTING

```
<160> NUMBER OF SEQ ID NOS: 68

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atttattact agacagagga                                                     20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aggcagagtt aattcgaaca                                                     20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
agactggtac aacaggactc                                                     20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cgcggtccaa cttaggcgta                                                     20

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tgagatctgg agaaaa                                                         16

<210> SEQ ID NO 6
```

```
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cttattaatt aacaga                                                       16

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gcggccgctt aattaa                                                       16

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ggatccgaat tcttgt                                                       16

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 9
ttttucaatg catcggtccc ggtattt                                           27

<210> SEQ ID NO 10
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10 attact                                                                   6

<210> SEQ ID NO 11
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11 agacag                                                                   6
```

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 12
aggaacggag gccgaacatg ctutttt                                      27

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(9)
<223> OTHER INFORMATION: a, c, t, g, unknown or other

<400> SEQUENCE: 13
agtaatnnnu accgggaccg augcattgut ttt                               33

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (25)..(27)
<223> OTHER INFORMATION: a, c, t, g, unknown or other

<400> SEQUENCE: 14
ttttuagcat gutcggcctc cgtunnnctg tct                               33

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 15
ttttucaatg catcggtccc ggtaggc                                      27

<210> SEQ ID NO 16
<211> LENGTH: 6
<212> TYPE: DNA
<213> ORGANISM: Artificial Sequence
<220> FEATURE:
<223> OTHER INFORMATION: Description of Artificial Sequence: Synthetic

```
            oligonucleotide

<400> SEQUENCE: 16 agagtt                                                                    6

<210> SEQ ID NO 17
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17 aattcg                                                                    6

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 18
aacaacggag gccgaacatg ctutttt                                            27

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(9)
<223> OTHER INFORMATION: a, c, t, g, unknown or other

<400> SEQUENCE: 19
aactctnnnu accgggaccg augcattgut ttt                                     33

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (25)..(27)
<223> OTHER INFORMATION: a, c, t, g, unknown or other

<400> SEQUENCE: 20
ttttuagcat gutcggcctc cgtunnncga att                                     33

<210> SEQ ID NO 21
<211> LENGTH: 27
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 21
ttttucaatg catcggtccc ggtagac                                        27

<210> SEQ ID NO 22
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22 tggtac                                                                6

<210> SEQ ID NO 23
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23 aacagg                                                                6

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
actcacggag gccgaacatg ctutttt                                        27

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(9)
<223> OTHER INFORMATION: a, c, t, g, unknown or other

<400> SEQUENCE: 25
gtaccannnu accgggaccg augcattgut ttt                                 33

<210> SEQ ID NO 26
<211> LENGTH: 33
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (25)..(27)
<223> OTHER INFORMATION: a, c, t, g, unknown or other

<400> SEQUENCE: 26
ttttuagcat gutcggcctc cgtunnncct gtt                                    33

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 27
ttttucaatg catcggtccc ggtcgcg                                           27

<210> SEQ ID NO 28
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28 gtccaa                                                                   6

<210> SEQ ID NO 29
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29 cttagg                                                                   6

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 30
cgtaacggag gccgaacatg ctutttt                                           27

<210> SEQ ID NO 31
<211> LENGTH: 33
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(9)
<223> OTHER INFORMATION: a, c, t, g, unknown or other

<400> SEQUENCE: 31
ttggacnnnu accgggaccg augcattgut ttt                                    33

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (25)..(27)
<223> OTHER INFORMATION: a, c, t, g, unknown or other

<400> SEQUENCE: 32
ttttuagcat gutcggcctc cgtunnncct aag                                    33

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 33
ttttucaatg catcggtccc ggttgaga                                          28

<210> SEQ ID NO 34
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34 tctgga                                                                   6

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gaaaaacgga ggccgaacat gct                                               23

<210> SEQ ID NO 36
<211> LENGTH: 57

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: modified_base
<222> LOCATION: (35)..(38)
<223> OTHER INFORMATION: a, c, t, g, unknown or other

<400> SEQUENCE: 36
ttttuagcat gutcggcctc cgtunnnntc cagannnnua ccgggaccga ugcattg    57

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 37
ttttucaatg catcggtccc ggtcttat    28

<210> SEQ ID NO 38
<211> LENGTH: 6
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 38 taatta    6

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 39
acagaacgga ggccgaacat gct    23

<210> SEQ ID NO 40
<211> LENGTH: 57
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide
<220> FEATURE:
<221> NAME/KEY: modified_base
<222> LOCATION: (25)..(28)
<223> OTHER INFORMATION: a, c, t, g, unknown or other
<220> FEATURE:

<221> NAME/KEY: modified_base
<222> LOCATION: (35)..(38)
<223> OTHER INFORMATION: a, c, t, g, unknown or other

<400> SEQUENCE: 40
ttttuagcat gutcggcctc cgtunnnnta attannnnua ccgggaccga ugcattg    57

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 41
ttttucaatg catcggtccc ggtgcggc                                    28

<210> SEQ ID NO 42
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42 cgctta                                                             6

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
attaaacgga ggccgaacat gct                                         23

<210> SEQ ID NO 44
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: modified_base
<222> LOCATION: (35)..(38)
<223> OTHER INFORMATION: a, c, t, g, unknown or other

<400> SEQUENCE: 44
ttttuagcat gutcggcctc cgtunnnnta agcgnnnnua ccgggaccga ugcattg    57

<210> SEQ ID NO 45
<211> LENGTH: 28
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 45
ttttucaatg catcggtccc ggtggatc                                          28

<210> SEQ ID NO 46
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46 cgaatt                                                                   6

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cttgtacgga ggccgaacat gct                                               23

<210> SEQ ID NO 48
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: modified_base
<222> LOCATION: (35)..(38)
<223> OTHER INFORMATION: a, c, t, g, unknown or other

<400> SEQUENCE: 48
ttttuagcat gutcggcctc cgtunnnnaa ttcgnnnnua ccgggaccga ugcattg           57

<210> SEQ ID NO 49
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: a, c, g or t

<400> SEQUENCE: 49 ggtctcn                                                                  7
```

-continued

```
<210> SEQ ID NO 50
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: a, c, g or t

<400> SEQUENCE: 50 cgtctcn                                                                  7

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
caatgcatcg gggtctctat ctg                                               23

<210> SEQ ID NO 52
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 52 gatcca                                                                   6

<210> SEQ ID NO 53
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 53
gatctagaga cccggaacat gct                                               23

<210> SEQ ID NO 54
<211> LENGTH: 52
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: misc_feature
<222> LOCATION: (20)..(23)
<223> OTHER INFORMATION: n is a, c, g, or t
<220> FEATURE:
<221> NAME/KEY: misc_feature
<222> LOCATION: (30)..(33)
<223> OTHER INFORMATION: n is a, c, g, or t
<220> FEATURE:
<221> NAME/KEY: modified_base
<222> LOCATION: (34)..(34)
```

```
<223> OTHER INFORMATION: a, c, t, g, unknown or other
<220> FEATURE:
<221> NAME/KEY: modified_base
<222> LOCATION: (46)..(46)
<223> OTHER INFORMATION: a, c, t, g, unknown or other

<400> SEQUENCE: 54
agcatgttcc gggtctcttn nnntggatcn nnntagagac cccgatgcat tg          52

<210> SEQ ID NO 55
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 55
caatgcatcg gggtctct                                                18

<210> SEQ ID NO 56
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 56
caatgcatcg gggtctctat ctggatccag atctagagac ccggaacatg ct          52

<210> SEQ ID NO 57
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(7)
<223> OTHER INFORMATION: a, c, t, g, unknown or other

<400> SEQUENCE: 57
agcatgttcc gggtctct                                                18

<210> SEQ ID NO 58
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 58
caatgcatcg gggtctct                                                18

<210> SEQ ID NO 59
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 59
atctagagac ccggaacatg ct                                           22

<210> SEQ ID NO 60
<211> LENGTH: 22
<212> TYPE: DNA
<213> ORGANISM: Artificial Sequence
```

```
<220> FEATURE:
<223> OTHER INFORMATION: Synthetic oligonucleotide
<220> FEATURE:
<221> NAME/KEY: modified_base
<222> LOCATION: (16)..(16)
<223> OTHER INFORMATION: a, c, t, g, unknown or other

<400> SEQUENCE: 60
agatagagac cccgatgcat tg                                    22

<210> SEQ ID NO 61
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(7)
<223> OTHER INFORMATION: a, c, t, g, unknown or other

<400> SEQUENCE: 61
agcatgttcc gggtctct                                         18

<210> SEQ ID NO 62
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 62
atctggatcc ag                                               12

<210> SEQ ID NO 63
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 63
agatctggat cc                                               12

<210> SEQ ID NO 64
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 64
caatgcatcg gggtctctat ctggatccag atctagagac ccggaacatg ct   52

<210> SEQ ID NO 65
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 65
caatgcatcg gggtctctag caggctcctg ttctagagac ccggaacatg ct   52

<210> SEQ ID NO 66
<211> LENGTH: 52
<212> TYPE: DNA
```

```
<213> ORGANISM: Artificial Sequence
<220> FEATURE:
<223> OTHER INFORMATION: Synthetic oligonucleotide

<400> SEQUENCE: 66
caatgcatcg gggtctctag caggatagca ttctagagac ccggaacatg ct        52

<210> SEQ ID NO 67
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 67
caatgcatcg gggtctctag caggatccag tactagagac ccggaacatg ct        52

<210> SEQ ID NO 68
<211> LENGTH: 52
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (46)..(46)
<223> OTHER INFORMATION: a, c, t, g, unknown or other

<400> SEQUENCE: 68
agcatgttcc gggtctctag atctggatcc agatagagac cccgatgcat tg        52
```